(12) United States Patent  (10) Patent No.: US 8,211,714 B2
Chait et al.  (45) Date of Patent: Jul. 3, 2012

(54) CHARACTERIZATION OF MOLECULES

(75) Inventors: Arnon Chait, Bay Village, OH (US);
Boris Y. Zaslavsky, Solon, OH (US)

(73) Assignee: Analiza, Inc., Bay Village, OH (US)

( * ) Notice: Subject to any disclaimer, the term of this patent is extended or adjusted under 35 U.S.C. 154(b) by 0 days.

(21) Appl. No.: 13/110,345

(22) Filed: May 18, 2011

(65) Prior Publication Data

US 2011/0218738 A1  Sep. 8, 2011

Related U.S. Application Data

(62) Division of application No. 10/293,959, filed on Nov. 12, 2002, now Pat. No. 7,968,350.

(60) Provisional application No. 60/336,895, filed on Nov. 12, 2001, provisional application No. 60/352,473, filed on Jan. 28, 2002, provisional application No. 60/361,661, filed on Mar. 4, 2002, provisional application No. 60/412,754, filed on Sep. 23, 2002.

(51) Int. Cl.
*G01N 33/536* (2006.01)
(52) U.S. Cl. ............... 436/536; 436/8; 436/63; 436/15; 435/4; 435/7.1; 435/7.4
(58) Field of Classification Search .................. None
See application file for complete search history.

(56) References Cited

U.S. PATENT DOCUMENTS

| 5,008,204 | A | 4/1991 | Stehling |
|---|---|---|---|
| 5,241,072 | A | 8/1993 | Colon et al. |
| 5,340,474 | A | 8/1994 | Kauvar |
| 5,734,024 | A | 3/1998 | Zaslavsky |
| 5,769,074 | A | 6/1998 | Barnhill et al. |
| 5,818,231 | A | 10/1998 | Smith |
| 5,948,750 | A | 9/1999 | Garsky et al. |
| 6,136,960 | A | 10/2000 | Chait et al. |
| 7,011,955 | B1 | 3/2006 | Stemmler et al. |
| 7,247,498 | B2 | 7/2007 | Godec et al. |
| 2001/0016590 | A1 | 8/2001 | Ahotupa et al. |
| 2001/0041353 | A1* | 11/2001 | McCarthy .............. 435/69.1 |
| 2002/0145425 | A1 | 10/2002 | Ebbels et al. |

(Continued)

FOREIGN PATENT DOCUMENTS

WO   WO 99/10522   3/1999

(Continued)

OTHER PUBLICATIONS

Albertsson, P.A. et al., English Language Abstract of "Separation processes in biotechnology," Bioprocess Technology, 1990, vol. 9, pp. 287-327.

(Continued)

*Primary Examiner* — N. C. Yang
(74) *Attorney, Agent, or Firm* — Wolf, Greenfield & Sacks, P.C.

(57) ABSTRACT

The invention involves obtaining signatures of species (including chemical, biological, or biochemical molecules) and/or signatures of interactions between species and using them to characterize species, characterize interactions, and/or identify species that could be useful in a variety of settings. Signatures can be obtained using aqueous multi-phase partitioning and can be used to predict molecular interactions for applications such as drug discovery. A plurality of aqueous multi-phase partitioning arrangements can define an overall system providing an information-intensive signature, maximizing precision and sensitivity.

17 Claims, 3 Drawing Sheets

U.S. PATENT DOCUMENTS

| | | | |
|---|---|---|---|
| 2003/0162224 | A1 | 8/2003 | Chait et al. |
| 2004/0229375 | A1 | 11/2004 | Chait et al. |
| 2004/0236603 | A1 | 11/2004 | Heller et al. |
| 2006/0240416 | A1 | 10/2006 | Banerjee et al. |
| 2006/0255257 | A1 | 11/2006 | Belgovskiy |
| 2006/0269964 | A1 | 11/2006 | Chait et al. |
| 2007/0128618 | A1 | 6/2007 | Chait et al. |
| 2008/0050831 | A1 | 2/2008 | Chait et al. |

FOREIGN PATENT DOCUMENTS

| | | |
|---|---|---|
| WO | WO 00/10674 | 3/2000 |
| WO | WO 01/55698 A1 | 8/2001 |
| WO | WO 03/016883 A1 | 2/2003 |
| WO | WO 03/042694 A2 | 5/2003 |
| WO | WO 2004/111655 A1 | 12/2004 |
| WO | WO 2005/008247 A2 | 1/2005 |
| WO | WO 2005/008247 A3 | 1/2005 |
| WO | WO 2006/124100 A2 | 11/2006 |
| WO | WO 2007/027561 A2 | 3/2007 |
| WO | WO 2008/005043 A2 | 1/2008 |

OTHER PUBLICATIONS

Andrews, A.T. et al. "Affinity gel electrophoresis as a predictive technique in the fractionation of transgenic sheep milk proteins by affinity aqueous two-phase partitioning," Biotechnology Letters, 2000, vol. 22, pp. 1349-1353.

Arnoldi et al., "Lipophilicity-Antifungal Activity Relationships for Some Isoflavonoid Phytoalexins," Journal of Agricultural and Food Chemistry, 1990, vol. 38, No. 3, pp. 834-838.

Atktinson, L. et al., "Trypsin and alpha-chymotrypsin partitioning in polyethylene glycol/maltodextrin aqueous two-phase systems," Food and Bioproducts Processing, 1994, vol. 72 (C2), pp. 106-112.

Berggren, K. et al., "Substitutions of surface amino acid residues of cutinase probed by aqueous two-phase partioning," Biochimica et Biophysica Acta, 2000, vol. 1481, pp. 317-327.

Bevan et al., "A High-Throughput Screening Method for the Determination of Aqueous Drug Solubility Using Laser Nephelometry in Microtiter Plates," Analytical Chemistry, Apr. 15, 2000, vol. 72, No. 8, pp. 1781-1787.

Bodnar et al., "Exploiting the Complementary Nature of LC/MALDI/MS/MS and LC/ESI/MS/MS for Increased Proteome Coverage," J. Am. Soc. Mass. Spectrom, 2003, vol. 14, pp. 971-979.

Chait, A. "From Structure to Signature," 8th Annual SBS Conference & Exhibition, Sep. 22-26, 2002, Netherlands Congress Centre, The Hague, The Netherlands.

Chait, A. "HTS Technology for Analysis of Structural Signatures of Biomolecules: Methodology and Applications," California Separation Science Society, WCBP 2002, 6th Symposium on the Interface of Regulatory and Analytical Sciences for Biotechnology Health Products, Jan. 27-30, 2002.

Durand et al., "Protein Glycosylation and Diseases: Blood and Urinary Oligosaccharides as Markers for Diagnosis and Therapeutic Monitoring," Clinical Chemistry, 2000, vol. 46, No. 6, pp. 795-805.

Everberg et al., "Protein pre-fractionation in detergent-polymer aqueous two-phase systems for facilitated proteomic studies of membrane proteins," J. Chromatogr., 2004, vol. 1029, pp. 113-124.

Guiliano, K.A., English Language Abstract of "Aqueous two-phase protein partitioning using textile dyes as affinity ligands," Analytical Biochemistry, 1991, vol. 197, No. 2, pp. 333-339.

Gulyaeva, N. et al., "Relative hydrophobicity of organic compounds measured by partitioning in aqueous two-phase systems," Journal of Chromatography B, 2000, vol. 743, pp. 187-194.

Guzzetta "Reverse Phase HPLC Basics for LC/MA" An IonSource Tutorial, published Jul. 22, 2001.

Harboe et al., "Generation of Antibodies to the Signal Peptide of the MPT83 Lipoprotein of Mycobacterium Tuberculosis," Scandinavian Journal of Immunology, Jan. 2002, vol. 55, No. 1, pp. 82-87.

International Preliminary Examination Report for PCT/US02/26019, filed Aug. 16, 2002.

International Search Report for PCT/US02/36519, dated Dec. 18, 2003.

International Search Report for PCT/US02/26019, filed Aug. 16, 2002.

International Search Report/Written Opinion for PCT/US2004/019343, filed Jun. 14, 2004, dated Nov. 23, 2004.

Kohwi et al., "Amphipathic Lipid-Bound Protein Antigents in Mouse Bladder Carcinomas Detected by a Monoclonal Antibody," Biochemestry, 1984, vol. 23, No. 25, pp. 5945-5950.

Kuboi, R. et al., English Language Abstract of "Evaluation of surface hydrophobicities of proteins using hydrophobic interaction with non-ionic surfactants in aqueous two-phase partitioning systems," Kagaku Kogaku Ronbunshu, 1993, vol. 19, No. 3, pp. 446-454.

Mueller et al., "Real and Pseudo Oxygen Gradients in Ca-alginate Beads Monitored During Polarographic PO-2-measurements using Pt-needle microelectrodes," Biotechnology and Bioengineering, 1994, vol. 44, No. 5, pp. 617-625.

Office Action from Canadian Application No. 2,466,663 dated May 6, 2010.

Office Action from Canadian Application No. 2,528,535 dated May 5, 2009.

Office Action from Canadian Application No. 2,528,535 dated Mar. 15, 2010.

Office Action from European Application No. 02768567 dated Mar. 24, 2009.

Office Action from European Application No. 02795636 dated Nov. 14, 2005.

Office Action from European Application No. 02795636 dated Feb. 8, 2007.

Office Action from European Application No. 02795636 dated Oct. 27, 2008.

Office Action from European Application No. 04776693.6 dated Oct. 15, 2007.

Office Action from European Application No. 04776693.6 dated Oct. 10, 2008.

Office Action from European Application No. 04776693.6 dated May 11, 2010.

Office Action from European Application No. 06851492 dated Mar. 31, 2009.

Office Action from U.S. Appl. No. 10/779,164 dated Jul. 31, 2009.
Office Action from U.S. Appl. No. 10/779,164 dated Feb. 25, 2010.
Office Action from U.S. Appl. No. 11/641,611 dated Sep. 1, 2010.
Office Action from U.S. Appl. No. 11/641,611 dated Jan. 5, 2011.
Office Action from U.S. Appl. No. 11/818,911 dated Jun. 23, 2010.
Office Action from U.S. Appl. No. 11/818,911 dated Dec. 6, 2010.

Peracaula et al., "Altered glycosylation pattern allows the distinction between prostate-specific antigen (PSA) from normal and tumor origins," Glycobiology, 2003, vol. 13, No. 6, pp. 457-470.

Platt, D.E. et al., "QSAR in grossly underdetermined systems: Opportunities and issues," IBM Journal of Research and Development, 2001, vol. 45 (web page).

Program listing of the Society of Biomoecular Screening 2002, Session 2A Technical Program for the 8th Annual SBS Conference & Exhibition, Sep. 22-26, 2002, Netherlands Congress Centre, The Hague, The Netherlands.

Program listing of the Society of Biomolecular Screening 2002 conference in the Hague, The Netherlands, Oct. 2002, pp. 1-3.

Program listing of the Well-Characterized Biologics Conference 2002, Jan. 29, 2002, pp. 1-44.

Program listing of the Well-Characterized Biologics Conference 2002, California Separation Science Society, WCBP 2002, 6th Symposium on the Interface of Regulatory and Analytical Sciences for Biotechnology Health Products, Jan. 27-30, 2002.

QSAR Introduction (web pages; pub. date unknown).

Richon, A. et al., "An Introduction to QSAR Methodology," (web page; pub. date unknown).

Sakurai, A. et al., English Language Abstract of "Ligand and nuclear factor-dependent change in hydrophobicity of thyroid hormone [beta]1 receptor," Thyroid, 1998, vol. 8, No. 4, pp. 343-352.

Schena et al., "Parallel human genome analysis: Microarray-based expression monitoring of 1000 genes," Proc. Natl. Acad. Sci., Oct. 1996, vol. 93, pp. 10614-10619.

Search Report from PCT/US2006/048344, filed Dec. 19, 2006, date of mailing Apr. 24, 2008.

Singh et al., "Gene expression correlates of clinical prostate cancer behavior," Cancer Cell, Mar. 2002, vol. 1, pp. 203-209.

Sniegoski, P. "An Examination of the Concentration of Organic Components Water-Extracted From Petroleum Products," Water Research, 1975, vol. 9, pp. 421-423.

Stovsky, M. et al., "PSA/SIA: A New Highly Sensitive and Specific Structure-Based Assay for Prostate Cancer" (poster), AUA NC 82nd Annual Meeting, Chicago, IL, Sep. 24-27, 2008.

Takano et al., "Measuring the Solubility of Liquid Organic Compounds in Water," Journal of the Chemical Society of Japan, 1985, vol. 11, pp. 2116-2119.

Takano et al. "Measuring the Solubility of Liquid Organic Compounds in Water" Journal of the Chemical Society of Japan, 1985, Vo. 11, pp. 2116-2119.

Written Opinion for PCT/US2006/048344, filed Dec. 19, 2006, date of mailing Apr. 24, 2008.

Written Opinion for PCT/US02/26019, filed Aug. 16, 2002.

Yan, X., "Detection by ozone-induced chemiluminescence in chromatography," Journal of Chromatography, 1999, vol. 842, pp. 267-308.

Zaslavsky, A. et al., "A New Method for Analysis of Components in a Mixture without Preseparation: Evaluation of the Concentration Ratio and Protein-Protein Interaction," Analytical Biochemistry, 2001, vol. 296, pp. 262-269.

Zaslavsky, Aqueous Two-Phase Partitioning (book), Marcel Dekker, NY, 1995.

Zaslavsky, J. "Characteristics of Protein-Aqueous Medium Interactions Measured by Partition in Aqueous Ficoll-Dextran Biphasic System," J. Chromatogr., 1983, vol. 260, pp. 329-336.

Office Action from U.S. Appl. No. 11/641,611 dated Apr. 5, 2011.

* cited by examiner

CHARACTERIZATION OF MOLECULES

RELATED APPLICATIONS

This application is a divisional of U.S. patent application Ser. No. 10/293,959, filed Nov. 12, 2002, which claims the benefit of priority under 35 U.S.C. §119(e) to the following U.S. provisional patent applications: Ser. No. 60/336,895, filed Nov. 12, 2001, Ser. No. 60/352,473, filed Jan. 28, 2002, Ser. No. 60/361,661, filed Mar. 4, 2002, and Ser. No. 60/412,754, filed Sep. 23, 2002 each of which is hereby incorporated herein by reference in its entirety.

FIELD OF THE INVENTION

The invention is generally related to characterization of physical and structural properties of molecules and interactions between molecules. More particularly, the invention is related to developing and using signatures obtained, for example, via aqueous multi-phase partitioning, which reflect structural and functional characteristics of biomolecules and/or molecules which interact with biomolecules.

BACKGROUND OF THE INVENTION

This invention relates generally to the analysis and characterization of biomolecules, complexes comprising biomolecules or analogous species thereof. The results of the analysis, represented as signatures, can be used to establish relationships between properties of large numbers of species which allows selection of species for specific uses based upon the correlation of the species' properties which have been analyzed and characterized using the methods of the invention.

Biomolecules are generally flexible three-dimensional (3-D) molecular structures. Members of one prototypical class of biomolecules, polypeptides, are normally constructed of a linear arrangement amino acids, i.e., they comprise amino acid sequences. The majority of amino acids which are contained in polypeptides are the 20 commonly-known amino acids. With proteins, as well as other biomolecules, the particular details of the 3-D structure of the protein is known to determine much of the biological information specific to a specific biomolecule. Typically, changes in the 3-D structure (conformation) are associated with a specific biological effect. In this sense, the state of conformation of a biomolecule must therefore reflect certain aspects of the biological information specific to the biomolecule.

It is generally recognized that the biological information of a specific biomolecule can be transferred to or from another species by non-covalent interactions between the specific biomolecule and the other species. Examples of such non-covalent interaction include binding events wherein the binding of a smaller molecule to the biomolecule induces changes in the conformation of the biomolecule. In many cases, as will be recognized by those of skill in the art, these changes in the conformation of the biomolecule can result in further changes in either the behavior or the characteristics of the biomolecules involved. These changes are often quite significant and include changes in what other biomolecules can be bound by the biomolecule. Series of events such as these are at the root of many specific biological effects. Therefore, analysis of biomolecular structures is of significant interest in the pursuit of effective therapies and improvements to biotechnology.

As it is generally practiced, structural analysis of biomolecules involves examination of structure at a number of levels of detail. For proteins, this includes analysis at the level of amino acid sequence (primary structure), secondary structure (e.g., alpha helix or beta sheet composition), tertiary structure (3-D detailed atomic structure), and quaternary structure (when the biomolecule is comprised of discrete sub-domains). Techniques to evaluate each of these aspects of structure are generally specific to the type of information desired. For example, the preferred methods for determining the primary sequence of a biomolecule are usually incapable of providing tertiary structural information and the techniques for providing tertiary structural information are ill-suited for determining primary sequence. Primarily, the methods and instrumentation that are available for analyzing higher order structure, namely, conformational information, are complex, slow, and difficult to perform. This is not surprising since detailed 3-D information involves, by definition, resolution of the type of atoms and their coordinates in space at the atomic scale. A different approach is needed to rapidly obtain useful higher order structural information with ease and simplicity.

Many biological processes are mediated by noncovalent binding interactions between a protein and another molecule. Examples of these include the participation of receptors, such as those for hormones, messengers and/or drugs, and the binding partners for the receptors, such as hormones, messengers, drugs and/or any other ligand. Such interactions and their role in mediating biological processes are well-known to those of skill in the art. Further, biological processes involving the interaction of one biomolecule with another are commonly recognized to include the interactions between different proteins. It is also recognized that the identification and characterization of interactions such as those described above is of great significance in the process of drug discovery and development. It is also recognized that methods for analyzing biochemical binding interactions, particularly for purposes of gaining insight regarding structural characteristics, require too much time and effort to be generally applied to larger numbers of potentially relevant or useful binding pairs.

Binding of a given receptor to its binding partner may be detected by a variety of techniques capable of monitoring changes in the physico-chemical features of the receptor induced by the binding or by those sensitive to the concentration of the unbound binding partner. The techniques based on the competition replacement of a specific ligand bound to the receptor by a binding partner are particularly popular in the art. Often, the specific ligand of interest is fluorescently or radioactively labeled. When this is done, the appearance of the ligand in a free unbound form resulting from its replacement in the complex with the receptor by a binding partner is readily monitored. However, these techniques are hampered by the fact that only compounds with the affinity for the receptor exceeding that of the specific ligand are capable of replacing the ligand in significant quantities and thereby allow its detection. Further, there are significant waste handling problems associated with the methods used to render a ligand detectable, i.e., radioactivity, toxicity.

In some cases, binding of a ligand is sufficient to change the function of a receptor. If so, then determination of ligand binding can also be used to determine that the function of the receptor has also changed, e.g., altered enzymatic activity or altered affinity for other biomolecules. In these cases, the quantification of ligand-receptor binding is suitable for screening compounds capable of affecting the receptor function and/or activity. However, such a simple approach is not always suitable or useful.

In many cases, binding of a particular ligand results in a specific alteration of the receptor activity and/or function, while binding of another ligand results in a different specific alteration of activity and/or function. These differences in the response to ligand binding depend upon the particular details of changes in the 3-D structure of the receptor (conformational changes). One example of this is the effect of different estrogenic compounds on the estrogen receptor. In this case, different compounds result in different, distinct conformational changes and these different changes result in different activity and/or function of the estrogen receptor. Thus, when screening a class of compounds for their effect on this receptor, or receptors with similar properties, any measure of affinity of ligand for receptor would not provide adequate information in regards to potential pharmacological activity of any compound. Further, the strength of the affinity is, in general, not correlated with the specific details of the conformational changes in the receptor. This lack of correlation between affinity and structure renders any predictive effort based on simple affinity characterization even less likely to succeed. However, the alternative, gaining conformational information that may be useful, is very difficult and expensive.

The experimental work required to characterize the state of conformation of a biomolecule, or of a complex containing a biomolecule such as a receptor-ligand complex, is extensive. Information about specific conformational changes may be obtained by indirect methods such as, but not limited to, spectroscopic, hydrodynamic, or immunogenic characterization of the receptor molecule. Alternatively, more direct methods such as, but not limited to, crystallization of the biomolecule or co-crystallization of the ligand-receptor complex followed by X-ray diffraction studies and NMR spectroscopy of the biomolecule or the ligand-receptor complex in solution, can be used.

The indirect methods generally detect a single property of the receptor molecule that may or may not be affected by the occurring conformational changes in any particular case. If a change is detected, it is often not particularly useful in monitoring what change in the conformational state has occurred, as it is only one-dimensional. Accordingly, for more complex molecules, the use of indirect techniques is often limited to monitoring systems that are already particularly well characterized.

The direct methods, particularly X-ray and NMR analysis, are the most definitive techniques for characterization of the 3-D structure of a biomolecule or of a receptor-ligand complex. But, like the indirect methods, the direct methods too have major limitations. Particularly, the direct methods require considerable amounts of time, are often unsuitable for studying large proteins (NMR), and require materials that are difficult to obtain, such as crystals of diffraction quality (X-Ray crystallography).

The biological effect of a specific ligand binding to a receptor can be determined by directly monitoring the cellular or physiological effects. While this will normally be required at some point during the development of any drug or pharmaceutical, studying biological effects directly is not a feasible means to screen the great many candidate drugs or potential targets that are currently available, or soon will be available. Simply stated, cell culture and animal trials are vastly too expensive in both time and resources to be applied to the large numbers of potential candidate compounds.

While many useful techniques for characterizing molecules exist, a need exists in the art for additional versatile, simple, powerful techniques for characterizing species (including chemical, biological, or biochemical species), characterizing structural aspects of species, characterizing interaction between various species, and the like.

SUMMARY OF THE INVENTION

The present invention provides a variety of techniques involving characterization of species, conformational aspects of species, interaction between species, and the like. A wide variety of the species including chemical species (such as small molecules), biological species such as proteins, and the like can be used in accordance with the invention, i.e., can realize benefits associated with the invention. In one aspect, the invention relates to a method for characterizing a species. In one embodiment, the method includes determining a relative measure of interaction between, at least, a species and a first interacting component and the species and a further interacting component, in a first system in which each of the first and second interacting components is able to interact with the species. The determining phase is repeated, with the species, in a second system including at least one different interacting component. The method also involves constructing, from relative measures of interaction of the species with interacting components in different systems, an interaction signature indicative of a property of the species. The property can be the molecular identity of the species, a conformational property of the species, a property of interaction between the species and at least one additional species, and/or other properties. The interacting components may contain, in addition to their constitutive components, also other molecules which may further interact with the species, e.g., formulation excipients, chaperon proteins, etc.

In another embodiment, the method involves providing a species, contacting the species with a first interacting component and at least one further interacting component. The components are selected so that the species can interact with each interacting component. The species and interacting components form a system. Further, the method involves determining a relative measure of interaction between the species and each interacting component and calculating a coefficient which defines the ratio of the relative measure of interaction between the species and the first interacting component and the relative measure of interaction between the species and the second interacting component.

In another aspect, the present invention relates to a method of characterizing structural states of more than one species. This method includes determining the signature of a first species, determining the signature of at least a second species, comparing the signature of the first species to the signature of further species and recording variances between the signature of the first species and the further species.

In another aspect, the present invention relates to a method for predicting the level of biological activity of interest of a biomolecule that is bound to a binding partner. Generally, this method involves obtaining reference signatures of biomolecules that are bound to other binding partners for which reference levels of biological activity of interest is known, obtaining the signature of the biomolecule bound to an experimental binding partner, comparing the signature of the biomolecule when bound to the experimental binding partner to data from earlier reference signatures, including use of any relationship derived in the practice of the invention, and predicting the biological activity of the experimental binding partner.

In another aspect, the present invention relates to a method of producing transformed signatures. This method includes determining a signature and representing the signature using mathematical or visual techniques. It further includes methods for comparing signatures. In certain aspects, this comparison includes expressing differences between signatures as mathematically-defined distances between the signatures.

In another aspect, the present invention relates to a method for determining a first and a second partition coefficient of a biomolecule. This aspect of the invention includes providing a first aqueous partitioning system, providing at least a second aqueous partitioning system, and contacting the biomolecule to be characterized with the first system and with further systems allowing separation of the phases. It further includes quantifying the concentration and/or relative concentration of biomolecule in the separated phases in the first system and in the further systems and then determining a partition coefficient, e.g., the ratio of biomolecule present in the separated phases, for the first system and for the further systems. The method can further include constructing a signature using a set of partition coefficients specific for the biomolecule.

In another aspect, the present invention relates to a method for determining a first and second partition coefficient of a species. This aspect of the method includes providing a first aqueous partitioning system, contacting the species to be characterized with the first system and with further systems, allowing separation of the phases, quantifying the concentration and/or relative concentration of the species in at least one separated phase in the first system and in the further systems and constructing a signature using the concentration of the species present in at least one separated phase in the first system and in the further systems.

In another aspect, the present invention relates to an apparatus for comparing signatures to reference signatures. The apparatus can include a memory that stores the signatures and identities of the species or groups of species that form a reference database and executable instructions. The apparatus includes a processor that executes instructions to receive a signature for a candidate species, to determine if the candidate species has a similar signature to species in the reference database and to output the results of the determination.

In another aspect, the present invention relates to computer-readable storage media which contains digitally-encoded signature data. The digitally-encoded signature data includes the identity and signature of biomolecules.

In another aspect, the present invention relates to a repository of reference signatures and software. Reference signature values in the repository of reference signatures can have a reference range of values indicating correlation. The software can be configured to receive an experimental subject set of values which make up an experimental signature, compare each subject set of values to the values of the reference signatures, where the reference signatures are correlated to activities or functions of interest and determine the proportion of experimental subject values that are within or outside the reference range of the reference values, thereby assigning a function or not to the experimental subject.

In another aspect of the invention, the structural state of a biomolecule bound to a binding partner can be used to predict biologically-related aspects of the structural state. The prediction of the biologically-related aspects of the structural state can include consideration of structural states of other biomolecules bound to binding partners and role of the structural states of other biomolecules in inducing biologically-related effects.

The invention, in one aspect, relates to methods for characterizing the structural state of a biomolecule or a mixture of biomolecules. The biomolecule(s) can be isolated or can be in solution with other species. The biomolecule(s) can be in direct contact mediated by non-covalent interactions with other species.

The characterization of the biomolecule(s) can include comparison to a reference state. The characterization can include comparison of the structure of the biomolecule(s) in a reference state to the structure when bound with a binding partner, when degraded, and when the structural state represents an average structural state resulting from a mixture of closely related biomolecules.

The subject matter of this application may involve, in some cases, interrelated products, alternative solutions to a particular problem, and/or a plurality of different uses of a single system or article.

Other advantages, features, and uses of the invention will become apparent from the following detailed description of non-limiting embodiments of the invention when considered in conjunction with the accompanying drawings, which are schematic and which are not intended to be drawn to scale. In the figures, each identical or nearly identical component that is illustrated in various figures typically is represented by a single numeral. For purposes of clarity, not every component is labeled in every figure, nor is every component of each embodiment of the invention shown where illustration is not necessary to allow those of ordinary skill in the art to understand the invention. In cases where the present specification and a document incorporated by reference include conflicting disclosure, the present specification shall control.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
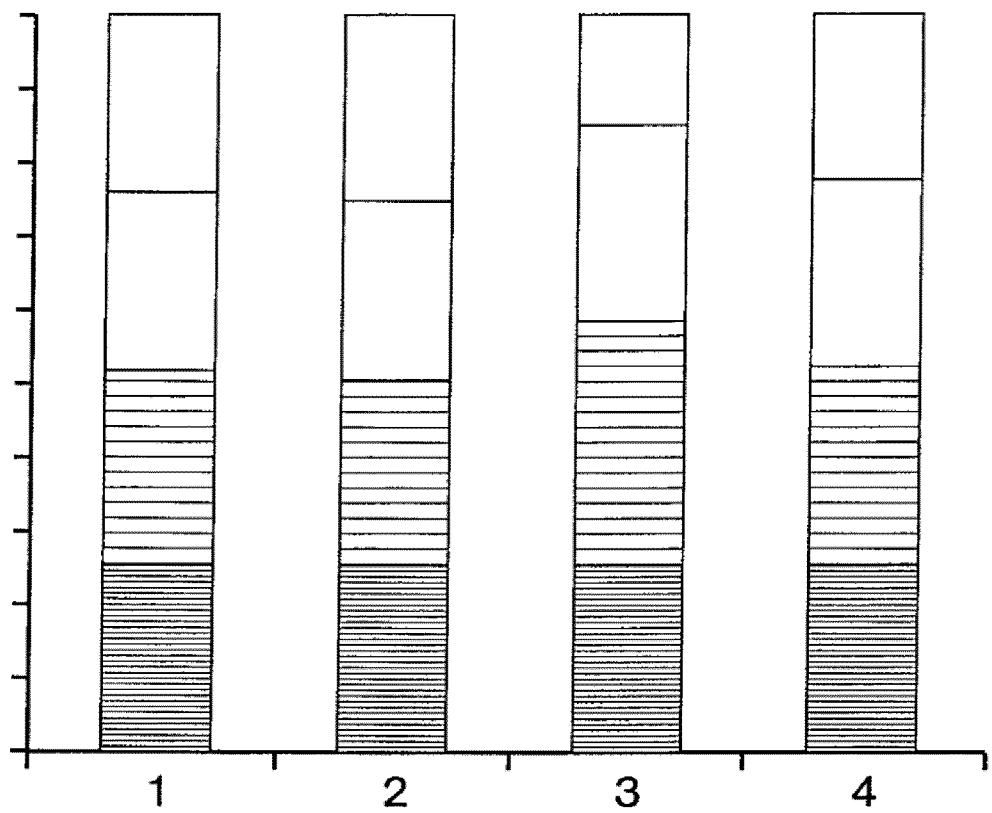
FIG. 1 is a visual representation of the signatures, using normalized bar graphs, whose numerical values are listed in Table 1. The values 1-4 on the abscissa refer to the PEG-phosphate, Dex-Ficoll, Dex-Ficoll-NaSCN, and Dex-PEG systems, respectively.

The present invention involves techniques for determining information about molecules and/or interactions between molecules. More particularly, the invention is related to developing and using signatures obtained, for example, via aqueous multi-phase partitioning, which reflect structural and functional characteristics of biomolecules or molecules which interact with biomolecules. These signatures can be used for the purposes of establishing relationships between structure and function or for the purposes of establishing functional and structural relationships to activity or to conditions.

Methods of the present invention can be useful for detecting, classifying, and/or predicting changes in the structure of biomolecules or molecules that interact with biomolecules. These changes can be changes in conformation or structure induced by primary sequence modification, by degradation of the biomolecule through chemical, thermal, or other degradation mechanisms, by interaction with other biomolecules, or by interaction with low molecular weight compounds.

Methods of the present invention can be used to analyze and/or characterize biological materials, including but not limited to, polypeptides, proteins, carbohydrates, nucleic acids, polynucleotides, lipids, sterols, and mixtures or derivatives thereof. It will be recognized by those of skill in the art that these biological materials can be found in the form of biopharmaceutical drug formulations, pharmaceutical drug formulations, extracts from natural sources, collections of molecules generated by combinatorial chemical or biochemical techniques and combinations thereof. Examples of behavior to be analyzed and/or characterized include, but are not limited to the detection and classification of conformational changes of receptors, detection of interactions between biomolecules, structural changes due to modification and combinations thereof.

Information gathered by application of these aspects of the invention is useful for screening potential drug candidates, for characterizing compounds in respect to toxicology concerns, for drug safely studies, for quality control, and for related purposes including basic research.

It is to be understood that this invention is not limited to specific methods, specific solutions, or to particular devices, as such may, of course, vary. It is also to be understood that the terminology used herein is for the purpose of describing particular embodiments only and is not intended to be limiting. Throughout the specification and claims, reference will be made to a number of terms which shall be defined to have the following meanings:

As used in the specification and the appended claims, the singular forms "a," "an" and "the" include plural referents unless the context clearly dictates otherwise. Thus, for example, reference to "a biomolecule" can include mixtures of a biomolecule, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

"Analyte," "analyte molecule," or "analyte species" refers to a molecule, typically a macromolecule, such as a polynucleotide or polypeptide, whose presence, amount, and/or identity are to be determined.

"Antibody," as used herein, means a polyclonal or monoclonal antibody. Further, the term "antibody" means intact immunoglobulin molecules, chimeric immunoglobulin molecules, or Fab or F(ab')$_2$ fragments. Such antibodies and antibody fragments can be produced by techniques well known in the art which include those described in Harlow and Lane (*Antibodies: A Laboratory Manual* Cold Spring Harbor Laboratory, Cold Spring Harbor, N.Y. (1989)) and Kohler et al. (*Nature* 256: 495-97 (1975)) and U.S. Pat. Nos. 5,545,806, 5,569,825 and 5,625,126, incorporated herein by reference. Correspondingly, antibodies, as defined herein, also include single chain antibodies (ScFv), comprising linked $V_H$ and $V_L$ domains and which retain the conformation and specific binding activity of the native idiotype of the antibody. Such single chain antibodies are well known in the art and can be produced by standard methods. (see, e.g., Alvarez et al., *Hum. Gene Ther.* 8: 229-242 (1997)). The antibodies of the present invention can be of any isotype IgG, IgA, IgD, IgE and IgM.

"Aqueous," as used herein, refers to the characteristic properties of a solvent/solute system wherein the solvating substance has a predominantly hydrophilic character. Examples of aqueous solvent/solute systems include those where water, or compositions containing water, are the predominant solvent.

"Aqueous multi-phase system," as used herein, refers to an aqueous system which consists of greater than one aqueous phase in which an analyte species can reside, and which can be used to characterize the structural state of the analyte species according to the methods described herein. For example, this includes aqueous system which can separate at equilibrium into two, three, or more immiscible phases. Aqueous multi-phase systems are known in the art and this phrase, as used herein, is not meant to be inconsistent with accepted meaning in the art.

An "interacting component" means a component, such as a phase of an aqueous multi-phase system, that can interact with a species and provide information about that species (for example, an affinity for the species). Multiple interacting components, exposed to a species, can define a system that can provide a "relative measure of interaction" between each component and the species. An interacting component can be aqueous or non-aqueous, can be polymeric, organic (e.g. a protein, small molecule, etc.), inorganic (e.g. a salt), or the like, or any combination. A set of interacting components can form a system useful in and in part defining any experimental method which is used to characterize the structural state of a species such as an analyte species according to the methods described herein. Typically, a system of interacting components can measure the relative interaction between the species and at least two interacting components. An aqueous multi-phase system is a species of a system of interacting components, and it is to be understood that where "Aqueous system" or "Aqueous multi-phase system" is used herein, this is by way of example only, and any suitable system of interacting components can be used.

Both aqueous two-phase and aqueous multi-phase systems, as used herein, also refer to systems analogous to those comprising only aqueous solutions or suspensions. For example, an aqueous two-phase system can include non-aqueous components in one or more phases that are not liquid in character. In this aspect, aqueous phase systems also refers to related techniques that rely on differential affinity of the biomolecule to one media versus another, wherein the transport of the biomolecule between one medium and, optionally, another medium occurs in an aqueous environment. Examples of such "heterogeneous phase systems" include, but are not limited to, HPLC columns or systems for liquid-liquid partition chromatography as are known to those of skill in the art.

"Partition coefficient," as used herein, refers to the coefficient which is defined by the ratio between the concentrations of the solute in the two immiscible phases at equilibrium. For example, the partition coefficient (K) of an analyte in a two-phase system is defined as the ratio of the concentration of analyte in the first phase to that in the second phase. For multi-phase systems, there are multiple partition coefficients wherein each partition coefficient defines the ratio of analyte in first selected phase and a second selected phase. It will be recognized that the total number of partition coefficients in any multi-phase system will be equal to the total number of phases minus one.

For heterogeneous phase systems, an "apparent partition coefficient," as used herein, refers to a coefficient which describes information obtained from alternative techniques which is correlated to the relative partitioning between phases. For example, if the heterogeneous two-phase system used is an HPLC column, this "apparent partition coefficient" can be the relative retention time for the analyte. It will be recognized by those of skill in the art that retention time of an analyte reflects the average partitioning of the analyte between a first, mobile phase and a second, immobile phase. Also, it will be recognized that other similarly determinable properties of analytes can also be used to quantify differences in physical properties of the analytes and are, therefore, suitable for use as apparent partition coefficients.

"Bind," as used herein, means the well understood receptor/ligand binding as well as other nonrandom association between an a biomolecule and its binding partner. "Specifically bind," as used herein describes a binding partner or other ligand that does not cross react substantially with any biomolecule other than the biomolecule or biomolecules specified.

Generally, molecules which preferentially bind to each other are referred to as a "specific binding pair." Such pairs include, but are not limited to, an antibody and its antigen, a lectin and a carbohydrate which it binds, an enzyme and its substrate, and a hormone and its cellular receptor. As generally used, the terms "receptor" and "ligand" are used to identify a pair of binding molecules. Usually, the term "receptor" is assigned to a member of a specific binding pair, which is of a class of molecules known for its binding activity, e.g., antibodies. The term "receptor" is also preferentially conferred on the member of a pair that is larger in size, e.g., on lectin in the case of the lectin-carbohydrate pair. However, it will be recognized by those of skill in the art that the identification of receptor and ligand is somewhat arbitrary, and the term "ligand" may be used to refer to a molecule which others would call a "receptor." The term "anti-ligand" is sometimes used in place of "receptor."

"Biomolecule," as used herein, means; peptides, polypeptides, proteins, protein complexes, nucleotides, oligonucleotides, polynucleotides, nucleic acid complexes, saccharides, oligosaccharides, carbohydrates, lipids and combinations, derivatives and mimetics thereof.

"Detectable," as used herein, refers the ability of a species and/or a property of the species to be discerned. One method of rendering a species detectable is to provide further species, that bind or interact with the first species, that comprise a detectable label. Examples of detectable labels include, but are not limited to, nucleic acid labels, chemically reactive labels, fluorescence labels, enzymic labels and radioactive labels.

"Mimetic," as used herein, includes a chemical compound, or an organic molecule, or any other mimetic, the structure of which is based on or derived from a binding region of an antibody or antigen. For example, one can model predicted chemical structures to mimic the structure of a binding region, such as a binding loop of a peptide. Such modeling can be performed using standard methods (see for example, Zhao et al., *Nat. Struct. Biol.* 2: 1131-1137 (1995)). The mimetics identified by methods such as this can be further characterized as having the same binding function as the originally identified molecule of interest according to the binding assays described herein.

Alternatively, mimetics can also be selected from combinatorial chemical libraries in much the same way that peptides are. (Ostresh et al., *Proc. Natl. Acad. Sci. USA* 91: 11138-11142 (1994); Domer et al., *Bioorg. Med. Chem.* 4: 709-715 (1996); Eichler et al., *Med. Res. Rev.* 15: 481-96 (1995); Blondelle et al., *Biochem. J.* 313: 141-147 (1996); Perez-Paya et al., *J. Biol. Chem.* 271: 4120-6 (1996)).

"Solid support," as used herein, means the well-understood solid material to which various components of the invention are physically attached, thereby immobilizing the components of the present invention. The term "solid support," as used herein, means a non-liquid substance. A solid support can be, but is not limited to, a membrane, sheet, gel, glass, plastic or metal. Immobilized components of the invention may be associated with a solid support by covalent bonds and/or via non-covalent attractive forces such as hydrogen bond interactions, hydrophobic attractive forces and ionic forces, for example.

"Heterogeneous aqueous systems," as used herein, refers to systems wherein in addition to an aqueous or largely aqueous component, there is also a largely non-aqueous component. The non-aqueous component can be capable of immobilizing or interacting with analytes. Examples of the non-aqueous component may include a solid support.

"Structure", "structural state", or "conformation," as used herein, all refer to the commonly understood meanings of the terms. Most specifically, the meaning of the terms as they apply to biomolecules such as proteins and nucleic acids, but also to pharmacologically active small molecules. In different contexts, the meaning of these terms will vary as is appreciated by those of skill in the art. For instance, the use of the terms; primary, secondary, tertiary or quaternary in reference to protein structure have accepted meanings within the art, which differ in some respects from their meaning when used in reference to nucleic acid structure (see Cantor & Schimmel, Biophysical Chemistry, Parts I-III). Unless otherwise specified, the meanings of these terms will be those generally accepted by those of skill in the art.

The structural state of a biomolecule, at whatever level of detail, can be affected by many different factors including, but not limited to; changes in the chemical composition of the biomolecule (e.g., addition, deletion or substitution of amino acids in proteins, covalent modification by chemical agents or cleavage by chemical or thermal degradation) and interactions with other biomolecules or with ligands. Evaluation of different structural states has been used as one of the primary methods to determine the potential effectiveness of different biomolecules.

As used herein, "signature" refers to a particular representation of desired information, which can be defined as a set of relative measures of interaction described above obtained from experiments with different interacting components. Typically, a signature is used in place of more detailed information when the latter is difficult to obtain, or when it is not necessary to completely describe such information in order to make use of it. For example, fingerprinting individual people is a well-recognized technique to uniquely identify an individual (to a reasonable certainty), providing a conveniently obtained and conveniently dense information set instead of describing the individual using other representations, e.g., genetic makeup, or by using exhaustively physical description and other information.

Similarly, signatures which disclose only a limited, but adequate description to provide identification, are routinely used in applications as diverse as radar signal identification of aircraft to stock market analyses. In the sciences, spectroscopic techniques exploit signature-based identification of chemical compounds, e.g., using near infrared spectra that are subsequently processed in a manner providing a fast and convenient way to identify a specific compound.

Each of the above-indicated examples illustrate much of what is required for a signature to be useful. First, it should correspond with the underlying information that it attempts to represent. Second, it generally is simpler to obtain than the underlying information from which it is derived. Third, it generally is simpler to manipulate and to understand than the underlying information. Consideration of these requirements and how they compare to current methods of characterizing biomolecules will indicate why developing signature systems for biomolecules is so desirable.

An "interaction signature," a used herein, means a signature characteristic of interaction of a species with at least one other species, optionally also characteristic of interaction of either or both species with another species or an environment (medium) in which the species exist and/or with which the species interact. For example, an interaction signature may characterize interaction of a species with one phase of a multi-phase system, and with another phase of the multi-phase system, with an overall interaction signature characteristic of the relative interaction of the species with the two (or more) phases. As further examples, an interaction signature can be characteristic of interaction of a species with any number of phases of a multi-phase system, and interaction signatures can exist for interaction between and among a variety of species and a variety of phases of a multi-phase system.

Conformational information of flexible biomolecules forms, at it core, a very complex set of data. A fully-represented 3D structure which indicates both the identity and coordinates of all constituent atoms comprising a biomolecule is simultaneously large, difficult to obtain, and often nearly incomprehensible. Thus, in the context of the present invention, a detailed 3-D representation of the actual conformation is not considered a signature but the underlying information. Sometimes it is necessary to obtain details of the conformation itself, e.g., for optimizing structures of ligands that interact with an active site of a receptor. However, for many, perhaps most, other applications such detailed information is neither necessary nor desirable. In those applications where highly detailed 3D structural information is not needed, what is needed is only a compact signature that subscribes to the three attributes detailed above.

In accordance with the desired attributes of a signature, an information set could be described by numbers, mathematical expressions, by visual representations or by other means that are known to those of skill in the art. The particular choice of how a signature is represented will primarily dependent upon the specific technique that is used to obtain the surrogate information that is used to construct the signature and on the manner in which the signature is ultimately going to be used. As will be recognized by those of skill in the art, many techniques have been developed to condense and convey information in a manner that would be suitable for use in establishing a signature or set of signatures.

Mathematical techniques suitable for obtaining a useful signature are numerous. They include, but are not limited to, linear or nonlinear mapping (e.g., artificial neural networks and partial least squares regression), matrix rotation and projection (e.g., principal component analysis and singular value decomposition), direct modeling using differential equations that reflect the underlying physical process, if the underlying physical process is known. Sometimes visual representations form superior signatures, especially if they readily convey the desired information, e.g., differences amongst individual sets, using shapes and colors which are easily conveyed to the observer.

Information sets to be used in generating signatures can comprise data from two or more trial or experimental conditions. In preferred embodiments, the method will use greater than 2, 3, 4, 5, 6, 8, 10 or 20 different sets of conditions. As will be recognized, the actual measurement or technique used to obtain a measurement is not limited to a specific technique. As described herein by way of example, the data can include partition coefficients or apparent partition coefficients. Other types of data and the means for obtaining the data therefor will also be recognized by those of skill in the art.

For example, aqueous two-phase partitioning can be used to gather information for generating a signature. Aqueous two-phase partitioning described in U.S. Pat. No. 6,136,960, hereby incorporated in its entirety, is one method by which information can be obtained for generating a signature. Partitioning of a biopolymer in aqueous two-phase systems depends on its three-dimensional structure and type and topography of chemical groups exposed to the solvent. Changes in the 3-D structure of a receptor induced by some effect, e.g., by binding of a ligand binding or by structural degradation, also change the topography of solvent accessible chemical groups in the biomolecule or both the topography and the type of the groups accessible to solvent. One result of these changes is an alteration in the partition behavior of the biomolecule or the ligand-bound-receptor. As a result, by monitoring the partition coefficient of an analyte, it is possible to detect a change in the state of a structure for which a partition coefficient is already known.

Similarly, such changes may be detected using other methods which have an underlying dependence upon the topography and/or the types of solvent accessible groups. Examples of such other methods include, but are not limited to, column liquid-liquid partition chromatography (LLCP), heterogeneous two-phase systems or a multiphase heterogeneous system. In these other cases, an apparent partition coefficient may be generated that expresses the relative changes in the average partitioning between a first and a second phase. For example, in LLPC, the retention volume of a receptor may be used as the apparent partition coefficient.

In cases where a method as in determining a coefficient which reflects a relative partitioning, whether it be a partition coefficient or an apparent partition coefficient, a single descriptor is obtained. This lends great simplicity and ease of use to the method, however as described above, single descriptors are not adequate to provide signatures. For, while the many different aqueous two-phase systems all differ in their sensitivity toward various chemical groups, e.g., charged and non-polar groups, the presence of a detectable difference between two conformational states, in the form of a change in a partition coefficient, may result from a great many different mechanisms. As such, a similar change in a single partition coefficient may reflect very dissimilar conformational changes. Alternatively, each partition coefficient can reflect multiple structural changes that compensate for one another. In a single, specific aqueous two-phase system, these compensating changes cannot be separated from one another. As a result, only a small part of the structural and conformational data which underlies the observed partition coefficient can be discerned with observation of biomolecules under a single condition. Consequently, a single partition coefficient does not provide a signature, but can be combined with other partition coefficients obtained under different conditions to provide a signature. Alternatively, apparent partition coefficients can be combined to provide a signature for a biomolecule.

Aqueous two-phase systems arise in aqueous mixtures of different water-soluble polymers or a single polymer and a specific salt. When two certain polymers, e.g., dextran (Dex) and polyethylene glycol (PEG), or a single certain polymer and a certain inorganic salt, e.g. polyvinylpyrrolidone (PVP) and sodium sulfate, are mixed in water above certain concentrations, the mixture separates into two immiscible aqueous phases. There is a discrete interfacial boundary separating two phases, one rich in one polymer and the other rich in the other polymer or inorganic salt. The aqueous solvent in both phases provides media suitable for biological products. Two-phase systems can be generalized to multiple phase system by using different chemical components, and aqueous systems with a dozen or more phases have been mentioned in the literature.

When a solute is introduced into such a two-phase system, it distributes between the two phases. Partitioning of a solute is characterized by the partition coefficient K defined as the ratio between the concentrations of the solute in the two immiscible phases at equilibrium. It was previously shown that phase separation in aqueous polymer systems results from different effects of two polymers (or a single polymer and a salt) on the water structure (B. Zavlaysky, Aqueous Two-Phase Partitioning: Physical Chemistry and Bioanalytical Applications, Marcel Dekker, New York, 1995). As the result of the different effects on water structure, the solvent features of aqueous media in the coexisting phases differ from one another. The difference between phases can be demonstrated by dielectric, solvatochromic, potentiometric, and partition measurements.

The basic rules of solute partitioning in aqueous two-phase systems were shown to be similar to those in water-organic solvent systems (Zavlaysky). However, what differences do exist in the properties of the two phases in aqueous polymer systems are very small relative to those observed in water-organic solvent systems, as should be expected for a pair of solvents of the same (aqueous) nature. Importantly, the small differences between the solvent features of the phases in aqueous two-phase or multi-phase systems can be modified so as to amplify the observed partitioning that results when certain structural features are present.

It is known that the polymer and salt compositions of each of the phases depend upon the total polymer and salt composition of an aqueous two-phase system. The polymer and salt composition of a given phase, in turn, governs the solvent features of an aqueous media in this phase. These features include, but are not limited to, dielectric properties, solvent polarity, ability of the solvent to participate in hydrophobic hydration interactions with a solute, ability of the solvent to participate in electrostatic interactions with a solute, and hydrogen bond acidity and basicity of the solvent. All these and other solvent features of aqueous media in the coexisting phases may be manipulated by selection of polymer and salt composition of an aqueous two-phase system. These solvent features of the media govern the sensitivity of a given aqueous two-phase system toward a particular type of solvent accessible chemical groups in the receptor. This sensitivity, type, and topography of the solvent accessible groups in two different proteins, for example, determine the possibility of separating proteins in a given aqueous two-phase system.

Currently the field lacks the theory capable to relate the polymer and salt composition of a system to the sensitivity of the aqueous media in the two phases toward different solvent accessible chemical groups in the biomolecules. This sensitivity is of paramount importance when, for example, subtle differences are being detected between the conformational changes in a receptor induced by binding of closely related chemical compounds. However, by utilizing a wide variety of different trial or experimental conditions to screen each biomolecule, signatures can be obtained reliably without the need to fully understand the underlying theory of aqueous two-phase partitioning, or any of the other related or substitutable techniques.

Also, by use of the concept of signature, one can overcome other problems in characterization of biomolecules. Particularly, evaluation of the conformational changes that are induced in a receptor by closely related ligands, or in a population of receptors with heterogeneity in their structures, or in the structure of a mixture of related biomolecules, is quite difficult to achieve. The reason that this is difficult to achieve reliably is that it is not that uncommon for there to be no net change in the molecular interactions between a population of biomolecules and the two solvents present for any given two-phase system. As a result, it is difficult to design a single two-phase system that can provide the necessary sensitivity towards all conformational changes that might be induced under a specific set of circumstances.

Information relating to the different conformation states of biomolecules can be of great use in assessing biological activity. For example, mixtures of closely related, but still heterogeneous, mixtures of biomolecules can have properties that are analogous to those described above for the populations of receptors and ligands, namely, individual species present in one mixture to the next can differ greatly from one another, but never be detected when using simple assays.

However, by application of the concept of signature to these mixtures of biomolecules, and comparing the results to that of a reference state, e.g., that corresponding to a directly measured biological activity level, a combination of simple assays can be used to monitor the levels of different heterogeneous components. These signatures can even be used to monitor the activity level of preparations.

Signatures can therefore be used for in-process monitoring of biotechnology products and for quality control of multi-component biopharmaceuticals, such as vaccines. They could also be used to compare production lot-to-lot variations, structural effects of excipients used during product formulation, etc. Further, signatures can be used as aids for the monitoring of diseased states, including diagnosing diseases and monitoring the response to treatment. Further signatures can be used for non-morphological evaluation of tissues and body fluids in pathological analysis.

Signatures can also be used to obtain information about conformational changes in biological receptors that are induced by the binding of ligands. In like manner, signatures can be used to identify and characterize the conformational effects of binding partners binding to one another.

The conformation information obtained by the use of the concept of signatures can be used to improve high throughput screening for drug discovery. For example, if one obtains 50 different compounds that bind to a potential target protein, one can rapidly find the change in the protein's signature for each of the 50 different compounds. This additional information can allow further analysis and comparison. If, in our example, one of the 50 compounds has a very unique signature, then it can be identified as being a compound which interacts with the target in a manner unique from the others. In another variation of this example, several drugs are already available together with their respective biological effects, and their signatures determined using the methods of the present invention. In this case new compounds that interact with the same biological receptor are sought with a preferred profile of biological effect similar to known drugs, but with, e.g., reduced side effects. In the present example the signatures of the 50 compounds that bind to the same target could be rapidly compared with those corresponding to the known drugs and only those whose signatures favorably correspond to the preferred drugs are promoted to further pharmaceutical development. Additionally, a set of profiles can be obtained for the same receptor bound to the same compound in different tissues. For example, estrogens bound to an estrogen receptor typically exhibit different degrees of biological activities in different body tissues, e.g., breast, bone, etc. The profile thus consists of the signature of a compound bound to the estrogen receptor now corresponding to multiple biological activity levels that could be expressed as a mathematical vector. Furthermore, the concept of a profile can also include the signatures of the same compound bound to different biological targets, e.g., to its receptor and to certain liver enzymes such as CYP-450. Thus the profile is expressed mathematically as a matrix of values, and is useful for, e.g., characterizing not only the biological activity but the potential liver toxicity of the compound. Such information is useful, as will be recognized by those of skill in the art.

Similarly, the use of signature can improve the discovery of protein-protein interactions, the analysis of excipients of biopharmaceutical drug formulations, and the manufacture of biological and biopharmaceutical agents. It will be recognized as an improvement as it can be used to both monitor and characterize effects of actions or agents on biomolecules. The information obtained by its use can also be used to improve processes relating to toxicology, forensic medicine, drug safety studies, and other related fields of biomedicine as will be recognized by those of skill in the art.

One method provided by the present invention is an improvement over previous methods for characterizing the structural state or changes in the structural state of a biomolecule. In particular, this method provides the means to obtain a signature which reflects a biological molecule or process of interest and which can be used to compare the biological molecule or process of interest to other reference biological molecules or processes.

The quantity of the biomolecule that is used for each experiment can be greater than 1, 2, 3, 5, 10, 15, 20, 30, 50, 100, 250, 400, 600 and 800 pico-, nano- or micrograms. The quantity of the biomolecule that is used for each experiment can be less than 2, 3, 5, 10, 15, 20, 30, 50, 100, 250, 400, 600, 800 and 1000 micro-, nano- or pico-grams. The volume of the experiment can be greater than 1, 2, 3, 5, 10, 15, 20, 30, 50, 100, 250, 400, 600 and 800 pico-, nano-, micro- or milliliters. The volume of each experiment can be less than 2, 3, 5, 10, 15, 20, 30, 50, 100, 250, 400, 600, 800 or 1000 pico-, nano-, micro-, or milliliters.

It will be appreciated by those skilled in the art that the particular volumes and amounts of protein or solution ingredients employed will vary without limitation according to the biomolecule, its concentration, and the desired experimental protocol.

Partitioning in the aqueous polymer two-phase systems is a highly efficient, versatile, and cost-effective method for detecting changes in a receptor induced by its binding to a binding partner. Aqueous two-phase systems arise in aqueous mixtures of different water-soluble polymers or a single polymer and specific salts. For example, dextran and polyethylene glycol ("PEG") are mixed in water above certain concentrations, the mixture separates into two immiscible aqueous phases separated by a clear interfacial boundary. These two separated phases are said to have resolved. In one phase, the solution is rich in one polymer and, on the other side of this boundary in a second phase, the solution is rich in the other polymer. The aqueous solvent in both phases provides media suitable for biological products such as proteins or for other biomolecules.

Selection and modification of the types, as reflected in, for example, the chemical nature, structure, and molecular weight, of the phase-forming polymers and the concentration of the polymers can be used to vary the properties of the phases. In addition, the composition of the phases can also be changed by the addition of inorganic salts and/or organic additives. Changes to the composition of the phases can alter the properties of the phases. Examples of types of aqueous two-phase systems that are useful for detecting and/or characterizing the binding of a binding partner to a receptor include, but are not limited to, dextran/PEG, dextran/polyvinylpyrrolidone, PEG/salt, and polyvinylpyrrolidone/salt.

Biomolecules such as proteins, nucleic acids or other also distribute between the two phases when placed into such a system. This partitioning of a biomolecule between the two phases is fairly simple. In some respects, it is similar to extraction as is normally in the chemical arts. For example, in the case where phase-forming polymers are used, solutions comprising one or more of the two polymers and the biomolecule are mixed together such that both phase-forming polymers and the biomolecule are mixed. The resulting solution is resolved and the two-phase system is formed. Optionally, centrifugation can be used to enhance separation of the phases. It will be recognized by those of skill in the art that partitioning behavior of a biomolecule may be influenced by many variables, such as the pH, the polymers used, the salts used, other factors relating to the composition of the system, as well as other factors such as temperature, volume, etc. Optimization of these factors for desired effects can be accomplished by routine practice by those of skill in the relevant arts in combination with the current disclosure.

Evaluation of data from partitioning of a biomolecule can involve use of the partition coefficient ("K"), which is defined as the ratio between the concentrations of the biomolecule in the two immiscible phases at equilibrium. For example, the partition coefficient, K, of a protein is defined as the ratio of the protein in first phase to that in the second phase in a biphasic system. When multiple phase systems are formed, there can be multiple independent partition coefficients that could be defined between any two phases. From mass balance considerations, the number of independent partition coefficients will be one less than the number of phases in the system.

It will be recognized that the partition coefficient K for a given biomolecule of a given conformation will be a constant if the conditions and the composition of the two-phase system to which it is subjected remain constant. Thus, if there are changes in the observed partition coefficient K for the protein upon addition of a potential binding partner, these changes can be presumed to result from changes in the protein structure caused by formation of a protein-binding partner complex. "K", as used herein, is used as specifically mathematically defined below, and in all instances also includes, by definition, any coefficient representing the relative measure of interaction between a species and at least two interacting components.

In order to determine the partition coefficient K of a protein or a mixture of a protein with another compound to be analyzed, concentrated stock solutions of all the components (polymer 1, e.g., dextran; polymer 2, e.g., PEG, polyvinylpyrrolidone, salts, etc.) in water can be prepared separately. The stock solutions of phase polymers, salts, and the protein mixture can be mixed in the amounts and conditions (e.g., pH from about 3.0 to about 9.0, temperature from about 4° C. to 60° C., salt concentration from 0.001 to 5 mole/kg) appropriate to bring the system to the desired composition and vigorously shaken. The system can then be allowed to equilibrate (resolve the phases). Equilibration can be accomplished by allowing the solution to remain undisturbed, or it can be accelerated by centrifugation, e.g., for 2-30 minutes at about 1000 to 4000 g or higher. Aliquots of each settled (resolved) phase can be withdrawn from both the upper and lower phases. The concentration of biomolecule can be determined for both the upper and lower phases.

Different assay methods may be used to determine the concentration of the biomolecules in each phase. The assays will depend upon the identity and type of biomolecule present. Examples of suitable assay techniques include, but are not limited to, spectroscopic, immunochemical, chemical, fluorescent, radiological and enzymatic assays. When the biomolecule is a peptide or protein, the common peptide or protein detection techniques can be used. These include direct spectrophotometry (monitoring the absorbance at 280 nanometers) and dye binding reactions with Coomassie Blue G-250 or fluorescamine, o-phthaldialdehyde, or other dyes and/or reagents. Alternatively, if the protein is either an antibody or an antigen, immunochemical assays can also be used.

The concentration of the biomolecule(s) in each phase can then be used to determine the partition coefficient, K, of the sample under the particular system conditions. Since K reflects only the ratio of the two concentrations, the absolute values are not typically required. It will be recognized that this can allow certain analytical procedures to be simplified, e.g., calibration can be eliminated in some instances.

The partition coefficient can then be compared with other K values. For example, a K value for a species can be compared to the K values for the species under different conditions, a K value for a species can be compared to the K values for the species when combined with other species, or a set of K values for a species can be compared to other sets of K values.

Additionally, if the biomolecule concentration in the two-phase system of a fixed composition is kept constant, the changes in the partition coefficient can be measured not as changes in the partition coefficient value, but as those in the biomolecule concentration in a given phase, for example, top phase of the system. This version of the procedure, as described in several examples below, can be more cost-, time- and labor-efficient than the determination of the partition coefficient value from measurements of the biomolecule concentrations in each phase of a system.

However, as described above, the partition coefficient of a single two-phase system could not be considered an adequate signature representation of the structural state of a biomolecule in many applications. Using a single two-phase system is possible, e.g., for comparison between two specific states of conformations representing a free versus a bound receptor. However, a higher dimensional signature is desirable, particularly as can be obtained from multiple aqueous two-phase systems that provide different solvent structures. Such systems can be formed with different pH values, different polymer types and molecular weight values, different ionic compositions, etc. Signatures that exhibit sensitivity towards different changes in the structure are, in general, formed by using K values from systems with significantly different solvent structures.

The use of multiple and different solvent structures to obtain a series of K values is an important advantage of the present invention that enables detection of general structural changes that otherwise could have self-canceled in one particular two-phase system. Similar advantages could be realized using one or more multiple-phase systems in which partitioning is accomplished simultaneously in multiple phases.

Once the set of partition coefficient values is obtained, the signature of the structure of the biomolecule, or of the biomolecule-ligand complex, or of the mixture of biomolecules is available as a set of numerical values. Multiple ways to further express this information are then available—the particular choice of which is primarily dependent upon the complexity of the set (e.g., how many K values are available?) and on the manner in which the signature is used (e.g., would simple visual representation suffice?). Different arrangements of this information and selection of those most suitable are within the skill of one of the art. One simple way to express the signature is to write down the K values for each case in a row. Different cases, corresponding to different structural states of the biomolecule in response to, e.g., different ligands, are written in sequential rows, with the columns representing the various aqueous systems that are used to construct the signature. In this case just described, the representation is a matrix of numbers that allows easy comparison of case against all other signatures. Alternatively, this information could be expressed visually, e.g., by using bar graphs for each state, where the location of each bar denotes a particular system and its height the actual value of K. If the range of K values obtained from a set of aqueous systems is large, it can be difficult to visually represent all of the values using linear abscissa scale. In such cases, it is easy to first transform the data using simple shift, logarithmic, or normalization operations.

One useful way to use the structural signature is to compare the structural states of a receptor that as it is bound to different ligands. If the ligand is a small molecule and the receptor is a much larger molecule, such as a protein, the signature can represent the structural state of the biomolecule alone. Furthermore, if certain ligands are known to produce certain biological responses, e.g., agonist vs. antagonist, the signatures of such receptors when bound to the known ligands can serve as examples for the use of classifying new ligands according to the similarity of their signatures to one or more of the known ligands. In another embodiment, different structural states of a biomolecule that have otherwise been characterized using other techniques can be represented via a set of signatures, and a comparison of an unknown structural state of the same biomolecule against the set of known signatures can be used to indicate the similarity of that unknown state to the previously characterized ones.

In yet another embodiment, signatures of mixtures of structurally similar biomolecules (isoforms) belonging to, e.g., biological active, partially active, or non-active structural states, can be obtained, and new samples or production lots of the same biomolecule mixture can be classified by how similar or dissimilar they are to previously known structural states that correspond to certain biological activity levels.

When the information conveyed by either the numerical or visual representations of the signature is rather large, e.g., if there are many aqueous systems and signatures to compare, certain information mapping techniques can be used to condense the amount of information without loss of generality, sensitivity, and specificity.

One particular embodiment that can be very useful when many signatures are available, and when numerical values, typically referred to as outputs can be assigned to each, representing, e.g., the degree of biological activity, includes the use of certain nonlinear mappings such as artificial neural networks. In such cases, the signatures can be expressed as the coefficients of the neural networks and are valid within the particular model, type, and network architecture. The power of such mappings is principally derived from their use: given a new signature of an unknown structural state in terms of the K values, it can readily be mapped into a predictive value of the desired output value. Furthermore, inverse optimization techniques can also be used with the already constructed mapping model to determine the desired set K values that correspond to a desired output value. The same techniques can be used to determine the sensitivity of the output to each K value. This information is particularly beneficial for trimming the set of systems, such as aqueous systems, to a minimum that is required to adequately represent the underlying structural information.

These mapping techniques could be represented, without a loss of generality, via the following equations:

$$\sum_{i=1}^{n} \left\{ \begin{array}{c} K_{i1} \\ K_{i2} \\ \vdots \\ \vdots \\ K_{il} \end{array} \right\}, \left\{ \begin{array}{c} BI_{i1} \\ BI_{i2} \\ \vdots \\ \vdots \\ BI_{im} \end{array} \right\} \Rightarrow \left\{ \begin{array}{c} C_1 \\ C_2 \\ \vdots \\ \vdots \\ C_m \end{array} \right\}$$

Where the symbol BI represents the biological index, e.g. activity level in a specific tissue, the symbol C is the coefficient that results from the mapping, the index n refers to the number of samples, the index m refers to the number of different biological activities related to the particular conformational state (e.g., in different tissues), and the index l refers to the number of K values (extent of the signature). Once the set of coefficients C (which could be as small as one, when only one biological activity level is relevant) is calculated, it could be used in reverse to predict the set of biological activity levels, BI, from the measured signature for an unknown compound, represented by its K values according to the reverse mapping:

$$\left\{ \begin{array}{c} K_1 \\ K_2 \\ \vdots \\ \vdots \\ K_l \end{array} \right\}, \left\{ \begin{array}{c} C_1 \\ C_2 \\ \vdots \\ \vdots \\ C_m \end{array} \right\} \Rightarrow \left\{ \begin{array}{c} BI_1 \\ BI_2 \\ \vdots \\ \vdots \\ BI_m \end{array} \right\}$$

Other techniques to condense the information space provided by the signatures are available. For example, matrix rotation and projection techniques are well known to those skilled in the art. Using principal component analysis and/or singular value decomposition, the information embedded in the signature can be optimally rotated and presented in, e.g., a set of eigenvalues of decreasing values corresponding to the principal components (eigenvectors). These eigenvalues could be expressed numerically or visually for each signature.

In one preferred embodiment of the present invention, only changes in the structural state are important. In such applications, it is sometimes sufficient to display the differences between a new signature and that corresponding to the reference state. In these applications, a null (zero) signature of the differences, if present, implies that the two states are similar. When a new signature is compared with a set of known signatures corresponding, e.g., to structural states of known biological activities in vivo produced by specific ligands, it is useful to define a measure of similarity of the new signature to the previous ones. This similarity could then be thought of, e.g., as the degree of closeness of the biological activity induced by the new ligand to other known ligands. More specifically, this embodiment can be used to rapidly classify, predict, or select new ligands for a well-studied biological receptor target, for which a plurality of drugs (ligands) already exist with known biological effects. The similarity of two or more signatures can be assessed and quantified using one or more of several distance measures, e.g., Euclidian distance. When ligands inducing known biological effects when bound to a specific biomolecules are available, a mathematical relationship can be constructed using mapping techniques. Once the mapping is known, a new ligand's activity level can be determined or classified using its signature and the relationship between the signature space and biological activity expressed via the mapping.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric pressure.

EXPERIMENTAL EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

In this example, the signature of a structural state of a biomolecule was created. The signature created can be shown numerically and visually. Binding of different ligands induced different conformational changes, which were then monitored to obtain signatures.

β-Lactoglobulin from bovine milk, retinol, nitrophenyl phosphate and bromoethanol were purchased from Sigma Chemical Company (St. Louis, Mo., USA) and used without further purification. A stock solution of β-lactoglobulin in water was prepared at a concentration of 10.0 mg/ml. Nitrophenyl phosphate, retinol, and bromoethanol were dissolved in the protein stock solutions in the molecular ratios as indicated in Table 1. These protein/binding partner solutions were subjected to partitioning in a series of different aqueous two-phase systems, also as indicated below.

The aqueous two-phase system contained 13.75 wt. % PEG-600 (molecular weight of about 600) and 21.00 wt. % sodium/potassium phosphate buffer (pH 6.8). Each system was prepared by mixing the appropriate amounts of stock polymer and buffer solutions dispensed by liquid handling workstation Hamilton ML-2200 into a 1.2 mL microtube. A total volume of 800 μL was dispensed to the microtube. A varied amount (40, 80, 120, 160, and 200 μL) of the β-lactoglobulin solution or that of a mixture of a given ratio and the corresponding amount (160, 120, 80, 40, and 0.0 μl) of water were added to a system. The ratio between the volumes of the two phases of each system of a final volume of 1.00 mL was as 1:1. The system was shaken vigorously and then centrifuged for 30 min. at about 4000 rpm to speed resolution of the two phases. Tubes were then taken from the centrifuge, aliquots of a given volume (100 μl for direct spectrophotometric analysis and 150 μl for fluorescence analysis) from the top and the bottom phases were withdrawn in duplicate. Each aliquot was diluted, mixed with appropriate reagents, and used for analyzed as described below.

The other aqueous two-phase system contained 8.88 wt. % Dextran-64 (molecular weight of about 64,000), 12.86 wt. % Ficoll-400 (molecular weight of about 400,000) and 0.01 M sodium phosphate buffer (pH 8.6). Each system was prepared by mixing the appropriate amounts of stock polymer and buffer solutions dispensed by liquid handling workstation Hamilton ML-2200 into a microtube of a total volume of 1.2 mL up to a total volume of a system of 820 μL. A varied amount (40, 80, 120, and 160 μl) of the β-lactoglobulin solution or that of a mixture of a given ratio and the corresponding amount (140, 100, 60, and 20 μl) of water were added to each system. The ratio between the volumes of the two phases of each system of a final volume of 1.00 mL was as 1:1. The system was shaken vigorously and centrifuged for 30 min. at about 4000 rpm to speed the resolution of the phases. Tubes were taken out of the centrifuge, and aliquots of a given volume (100 μl for direct spectrophotometric analysis and 150 μl for fluorescence analysis) from the top and the bottom phases were withdrawn in duplicate and each diluted and mixed with appropriate reagents as indicated below and used for further analysis performed as described below.

The other aqueous two-phase system contained 10.98 wt. % Dextran-64 (molecular weight of about 64,000), 15.95 wt. % Ficoll-400 (molecular weight of about 400,000), 0.24M NaSCN, and 0.01 M sodium phosphate buffer (pH 8.6). Each system was prepared by mixing the appropriate amounts of stock polymer, salt, and buffer solutions dispensed by liquid handling workstation Hamilton ML-2200 into a microtube of a total volume of 1.2 mL up to a total volume of a system of 920 μL. A varied amount (20, 40, 60, and 80 μl) of the β-lactoglobulin solution or that of a mixture of a given ratio and the corresponding amount (60, 40, 20, and 0 μl) of water were added to a system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. Tubes were taken out of the centrifuge, and aliquots of 100 μl for direct spectrophotometric analysis from the top and the bottom phases were withdrawn in duplicate and each diluted and mixed with appropriate reagents as indicated below and used for further analysis performed as described below.

The other aqueous two-phase system contained 12.33 wt. % Dextran-64 (molecular weight of about 64,000), 6.05 wt. % PEG-6000 (molecular weight of about 6,000), 0.15M NaCl, and 0.01 M sodium phosphate buffer (pH 7.4). Each system was prepared by mixing the appropriate amounts of stock polymer, salt, and buffer solutions dispensed by liquid handling workstation Hamilton ML-2200 into a microtube of a total volume of 1.2 mL up to a total volume of a system of 800 μL. A varied amount (50, 100, 150, and 200 μl) of the β-lactoglobulin solution or that of a mixture of a given ratio and the corresponding amount (150, 100, 50, and 0 μl) of water were added to a system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. Tubes were taken out of the centrifuge, and aliquots of 100 μl for direct spectrophotometric analysis from the top and the bottom phases were withdrawn in duplicate and each diluted and mixed with appropriate reagents as indicated below and used for further analysis performed as described below.

For direct spectrophotometric analysis aliquots of 100 μl from the top and the bottom phases were withdrawn in duplicate and each mixed with 800 μl water. The protein concentrations in each phase were assayed by measuring the optical absorbance at 278 nm with a UV/VIS spectrophotometer HP-8530. The measured optical absorbance at 278 nm values of the diluted aliquots from the top phases were plotted as a function of the optical absorbance at 278 nm values of the similarly diluted aliquots from the bottom phases. The partition coefficient for the protein was determined as a slope of the linear curve representing the plot.

In addition, the protein concentrations in each phase were assayed by measuring the relative fluorescence intensity in wells of a 96-well microplate with a fluorescence microplate reader Bio-Tek F-6000 using excitation filter at 360 nm and emission filter at 460 nm. For this purpose aliquots of 50 μl from the top and the bottom phases were withdrawn, each mixed with 500 μl borate buffer, pH 8.4 and 75 μl fluorescamine solution (0.1 mg/ml) in acetone, maintained at ambient temperature for 15 min and used for further analysis. Aliquots of the mixtures (250 μl) were placed into wells of a microplate for fluorescence measurements. The measured fluorescence intensities of the aliquots from the top phases were plotted as a function of the fluorescence intensities of the aliquots from the bottom phases. The partition coefficient for a given protein was determined as a slope of the linear curve representing the plot.

The partition experiments were carried out in duplicate or triplicate. The partition coefficient values determined with two different assays agreed within 2-3% error range in each case. The partition coefficients for the examined mixtures of β-lactoglobulin and its binding partners are presented in Table 1.

Analysis of the data presented in Table 1 indicates that the partition coefficient K values for the protein changes in the presence of each ligand examined in almost all the systems (except in the presence of bromethanol in the Dex-PEG system). However, if only one system would have been used for analysis of the conformational changes induced by the ligand binding, inadequate conclusions might have been drawn. For example, binding of retinol acetate increases the K value of the protein in PEG-Phosphate, Dex-PEG, and Dex-Ficoll-NaSCN systems used, and reduces the K-value in the Dex-Ficoll system employed. At the same time binding of nitrophenyl phosphate and bromethanol decreases the protein K-value in all the systems used here.

TABLE 1

Partition coefficients, K, of bovine β-lactoglobulin with different binding partners in the indicated aqueous two-phase systems (protein:binding partner molecular ratio 1:1 in each case).

| Binding Partner | System: | | | |
| --- | --- | --- | --- | --- |
| | PEG/Phosphate K-value | Dex-Ficoll K-value | Dex-Ficoll-NaSCN K-value | Dex-PEG K-value |
| None | 1.796 ± 0.005 | 0.836 ± 0.003 | 0.451 ± 0.002 | 0.180 ± 0.008 |
| Retinol acetate | 1.858 ± 0.016 | 0.812 ± 0.006 | 0.468 ± 0.002 | 0.196 ± 0.001 |

TABLE 1-continued

Partition coefficients, K, of bovine β-lactoglobulin with different binding partners in the indicated aqueous two-phase systems (protein:binding partner molecular ratio 1:1 in each case).

| Binding Partner | System: | | | |
| --- | --- | --- | --- | --- |
|  | PEG/Phosphate K-value | Dex-Ficoll K-value | Dex-Ficoll-NaSCN K-value | Dex-PEG K-value |
| Nitrophenyl phosphate | 1.714 ± 0.012 | 0.823 ± 0.018 | 0.420 ± 0.001 | 0.103 ± 0.001 |
| Bromoethanol | 1.904 ± 0.013 | 0.848 ± 0.009 | 0.486 ± 0.005 | 0.183 ± 0.001 |

Systems compositions are described in the text.

This example illustrates that the use of a series of different aqueous two-phase systems significantly improves our ability to describe the conformational changes induced in a protein by binding of different ligands. Different systems to be used for the purpose of the present invention, as shown in this example, may include those formed by a single polymer and inorganic salt(s), by different pairs of polymers, and by the same pair of polymers and different salt additives. The analytical assay technique used for the determination of the receptor concentration may also be different—in this case using fluorescamine-based assay provided results identical to those obtained with direct absorbance measurements at ~280 nm.

The signature of the state of the structure in the present example can be expressed in a variety of ways. For example, a visual representation of the information in Table 1 can be constructed by first normalizing the K values obtain for each system by the largest value, then displaying the resulting matrix in graphical form. This was done and the results are shown in FIG. 1. In this particular graphical representation, the height of each bar is equal, and the relative contribution of each system to each bar height is denoted by its vertical extent. Also, the signature of each structural state is understood as the pattern obtained for the four cases (shown on the abscissa) by the assembly of bars, wherein the height of each sub-section corresponding to the normalized K value at a different aqueous system.

Example 2

In this example, it was demonstrated how to use a structural signature to discern between specific versus non-specific binding of ligands to a biomolecule by observing the structural signatures of the conformational state that is induced by such binding.

Lysozyme from hen egg white, N,N'-diacetylchitobiose and N,N',N''-triacetylchitotriose were purchased from Sigma Chemical Company (St. Louis, Mo., USA) and used without further purification. Glucose and N-acetyl-D-glucosamine were purchased from USB Corporation (Cleveland, Ohio, USA) and used without further purification. Stock solutions of lysozyme in water were prepared at a concentration of 5.0 mg/ml. N,N'-Diacetylchitobiose and N,N',N''-triacetylchitotriose were dissolved at a concentration of 10 mg/ml and mixed with the protein solution in ratios appropriate to provide protein:ligand molecular ratios of 1:1. Stock solutions of lysozyme and of the lysozyme mixtures with ligands were added to an aqueous two-phase system as described below.

The aqueous two-phase system contained 12.33 wt. % Dextran-64 (molecular weight of about 64,000), 6.05 wt. % PEG-6000 (molecular weight of about 6,000), 0.15M NaCl, and 0.01 M sodium phosphate buffer (pH 7.4). Each system was prepared by mixing the appropriate amounts of stock polymer, salt, and buffer solutions dispensed by liquid handling workstation Hamilton H-2200 into a microtube of a total volume of 1.2 mL up to a total volume of a system of 800 μL. A varied amount (50, 100, 150, and 200 μl) of the lysozyme solution or that of a mixture of lysozyme with a ligand and the corresponding amount (150, 100, 50, and 0 μl) of water were added to a system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. Tubes were taken out of the centrifuge, and aliquots of 100 μl for direct spectrophotometric analysis from the top and the bottom phases were withdrawn in duplicate and each diluted and mixed with appropriate reagents as indicated below and used for further analysis performed as described below.

The other aqueous two-phase system contained 8.88 wt. % Dextran-64 (molecular weight of about 64,000), 12.86 wt. % Ficoll-400 (molecular weight of about 400,000) and 0.01 M sodium phosphate buffer (pH 8.6). Each system was prepared by mixing the appropriate amounts of stock polymer and buffer solutions dispensed by liquid handling workstation Hamilton H-2200 into a microtube of a total volume of 1.2 mL up to a total volume of a system of 820 μL. A varied amount (40, 80, 120, and 160 μl) of the lysozyme solution or that of a mixture of lysozyme with a ligand (140, 100, 60, and 20 μl) of water were added to each system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. The tubes were taken out of the centrifuge, aliquots of a given volume (100 μl for direct spectrophotometric analysis and 150 μl for fluorescence analysis) were removed from the top and the bottom phases in duplicate and each aliquot was diluted and mixed with appropriate reagents and used for further analysis performed as described below.

The other aqueous two-phase system contained 8.88 wt. % Dextran-64 (molecular weight of about 64,000), 12.86 wt. % Ficoll-400 (molecular weight of about 400,000), 0.25 M $Na_2SO_4$, and 0.01 M sodium phosphate buffer (pH 8.6). Each system was prepared by mixing the appropriate amounts of stock polymer, salt, and buffer solutions dispensed by liquid handling workstation Hamilton H-2200 into a microtube of a total volume of 1.2 mL up to a total volume of a system of 910 μL.

A varied amount (20, 40, 60, and 90 μl) of the lysozyme solution or that of a mixture of lysozyme with a ligand and the corresponding amount (70, 50, 30, and 0 μl) of water were added to a system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. Tubes were taken out of the centrifuge, and aliquots of 100 μl for direct spectrophotometric analysis from the top and the bottom phases were withdrawn in duplicate and each diluted and mixed with appropriate reagents as indicated below and used for further analysis performed as described below.

For direct spectrophotometric analysis aliquots of 100 μl from the top and the bottom phases were withdrawn in duplicate and each mixed with 800 μl water. The protein concentrations in each phase were assayed by measuring the optical absorbance at 278 nm with a UV/VIS spectrophotometer HP-8530. The measured optical absorbance at 278 nm values of the diluted aliquots from the top phases were plotted as a function of the optical absorbance at 278 nm values of the similarly diluted aliquots from the bottom phases. The partition coefficient for the protein was determined as a slope of the linear curve representing the plot.

The protein concentrations in the top phases were assayed by measuring the relative fluorescence intensity in wells of a 96-well microplate with a fluorescence microplate reader Fluorolite-1000 using excitation filter at 405 nm and emission filter at 480 nm. The measured fluorescence intensities of the aliquots from the top phases were plotted as a function of the volume of protein solution added to a system. The concentrations of a given protein/binding partner pair in the top phase was determined as a slope of the linear curve representing the plot. The partition experiments were carried out in duplicate or triplicate.

The partition coefficient values for the examined mixtures of lysozyme and its binding partners are presented in Table 2.

corresponds to a particular system), one is able to discriminate more easily between what would otherwise appear to be similar data.

Figure 3:
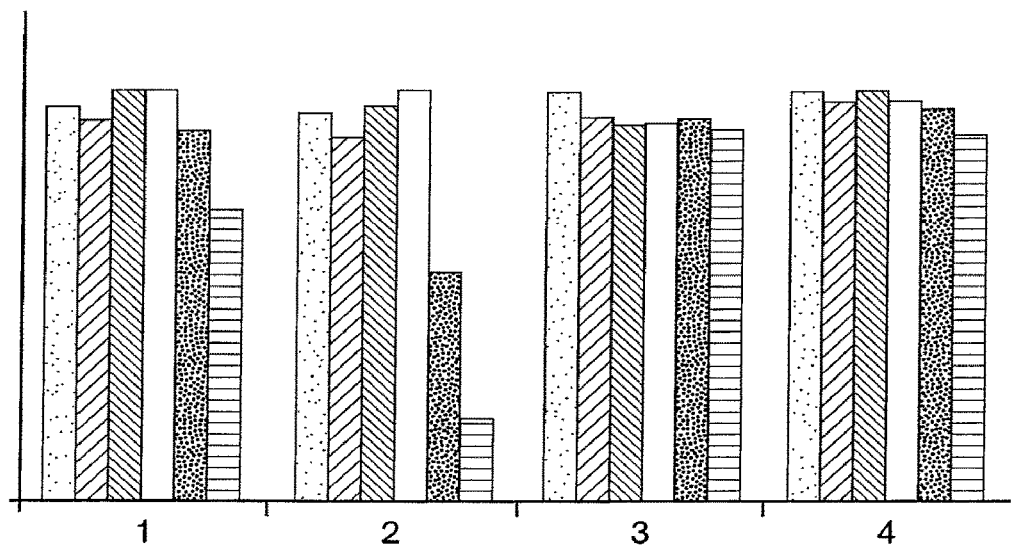
FIG. 3 is a visual representation of the relative contribution of each system to the signatures whose numerical values are listed in Table 2. The values 1-4 on the abscissa refer to the Dex-PEG, PEG-3350-phosphate, Dex-Ficoll, and Dex-Ficoll-$Na_2SO4$ systems, respectively.

In this particular representation of the signature, non-specific binding events were recognized as those which do not result in significant visual (or numerical) deviations from the signature of the free receptor alone, while the three ligands that are known to be of an increased degree of specificity (from N to N,N' to N,N', N''', respectively) produced signature that increasingly deviate from that of the free receptor. However, by using the graphical representations of the signature it was also easy to determine with component of the signature did not provide information useful to the providing a useful signature. For a signature to be useful, it must provide one-to-one correspondence with the underlying information, even if the basis by which the underlying information gives rise to the signature is not known. Thus, if we plot, e.g., the variation of the components of all the signatures for each system separately (FIG. 3), it becomes evident that the last two systems (Dex-Ficoll-NaSCN and Dex-PEG) are less useful for discerning structural differences amongst the different ligands.

Example 3

In this example, it was shown how sensitive conformational information can be obtained using a signature and how different states of the structure of biomolecules can be compared against a reference state. It was also demonstrated how to condense the difference between the signatures of a different conformation into a simple numerical value. Further, sev-

TABLE 2

Partition coefficient values for hen egg white lysozyme and its mixtures with different binding partners in different aqueous two-phase systems (molar ratio lysozyme:ligand = 1:1 in each case).

| | System: | | | |
|---|---|---|---|---|
| Binding Partner | Dex-PEG K-value | PEG-3350-Phosphate K-value | Dex-Ficoll K-value | Dex-Ficoll-Na2SO4 K-value |
| None | 2.728 ± 0.010 | 2.278 ± 0.006 | 0.890 ± 0.007 | 1.239 ± 0.008 |
| Glucose | 2.645 ± 0.025 | 2.119 ± 0.035 | 0.829 ± 0.005 | 1.206 ± 0.024 |
| Mannose | 2.848 ± 0.028 | 2.311 ± 0.022 | 0.811 ± 0.005 | 1.236 ± 0.012 |
| N-Acetyl-D-glucosamine | 2.860 ± 0.035 | 2.402 ± 0.002 | 0.818 ± 0.003 | 1.214 ± 0.010 |
| N,N'-Diacetylchitobiose | 2.563 ± 0.032 | 1.311 ± 0.013 | 0.826 ± 0.001 | 1.177 ± 0.009 |
| N,N',N''-Triacetylchitotriose | 2.033 ± 0.052 | 0.461 ± 0.006 | 0.803 ± 0.004 | 1.106 ± 0.007 |

This example illustrates that binding of nonspecific ligands, such as glucose and mannose, results in changes in the partition coefficient that can be distinguished from binding of specific ligands. Specifically, in this example, the changes in the protein partition coefficient value did not exceed 5%, while binding of specific ligands at the active site of lysozyme resulted in partition coefficient changes ranging from 6% up to 80% depending on the particular aqueous two-phase system. Further, the example demonstrates that the sets of partition data, like that in Table 2, and analysis of patterns of partition behavior of protein-ligand complexes in a set of different two-phase systems, provides information of greater reliability and quality that one would expect from a collection of single two-phase signatures.

Figure 2:
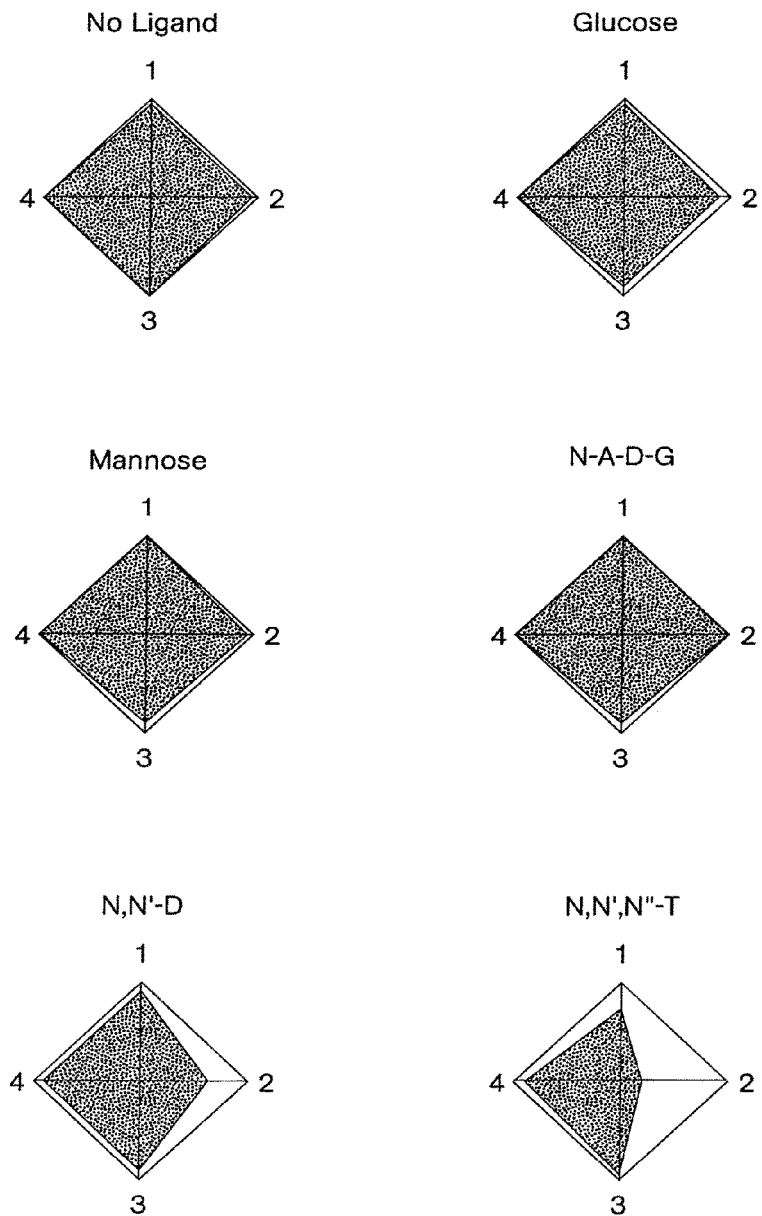
FIG. 2 is a visual representation of the signatures, using normalized radar plots, whose numerical values are listed in Table 2. The values 1-4 in each of the radar plots refer to the Dex-PEG, PEG-3350-phosphate, Dex-Ficoll, and Dex-Ficoll-$Na_2SO4$ systems, respectively.

For example, evaluation of a one-dimensional signature represented by the partition coefficient in the Dex-Ficoll system does not clarify the types of conformational modifications that are induced by each ligand. However, by using the entire information set as a multi-dimensional signature, e.g., visually as provided in FIG. 2 using the normalized values of the partition coefficient in a radar plot (where each vertex eral representative applications for such condensed information sets which reflect differences between signatures are disclosed.

Apo-transferrin from human serum was purchased from Intergen Company (Purchase, N.Y., USA) and used without further purification. Apo-transferrin was saturated with iron ($Fe^{3+}$), copper ($Cu^{2+}$), aliminium ($Al^{3+}$), bismuth ($Bi^{3+}$), and calcium ($Ca^{2+}$) according to the standard procedure by incubation on ice for 1 hour with triplicate molar excess of $FeCl_3$, or $CuCl_2$, $Al_2(SO_4)_3$, $Bi_6Mo_2O_{15}$, and $CaCl_2$ in the presence of sodium salt of nitriloacetic acid in 0.5 M Tris-HCl buffer, pH 8.5, and an excess of bicarbonate. The unbound metal salt was removed from each solution of the metal-saturated transferring by centrifugation of the solution in a MACROSEP centrifugal concentrator with the molecular weight cutoff 3K for about 4 hrs at 3,000 g. After that, stock solutions of metal-saturated transferrins and apo-transferrin in water were prepared at the protein concentration of ca. 10 mg/ml. These protein solutions were subjected to partitioning in the following aqueous two phase systems.

The aqueous two-phase system contained 3.60 wt. % PEG-8000, 7.74 wt. % dextran-500 (with molecular weight of about 500,000), and 0.20 M sodium phosphate buffer (pH 7.01). Each system was prepared by mixing the appropriate amounts of stock polymer, salt, and buffer solutions dispensed by liquid handling workstation Hamilton ML-2200 into a microtube of a total volume of 1.2 mL up to a total volume of a system of 700 µL. A varied amount (100, 150, 200, 250, and 300 µl) of the apo-transferrin solution or that of a metal-transferrin and the corresponding amount (200, 150, 100, 50, and 0 µl) of water were added to a system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. Tubes were taken out of the centrifuge, and aliquots of 100 µl for direct spectrophotometric analysis from the top and the bottom phases were withdrawn in duplicate and each diluted and mixed with appropriate reagents as indicated below and used for further analysis performed as described below.

The other aqueous two-phase system contained 20.00 wt. % polyvinylpyrrolidone (PVP), 6.19 wt. % dextran-500 (with molecular weight of about 500,000), and 0.1725 M sodium phosphate buffer (pH 7.4). Each system was prepared by mixing the appropriate amounts of stock polymer and buffer solutions dispensed by liquid handling workstation Hamilton H-2200 into a microtube of a total volume of 1.2 mL up to a total volume of a system of 750 µl. A varied amount (50, 100, 150, 200, and 250 µl) of the apo-transferrin solution or that of a metal-transferrin and the corresponding amount (200, 150, 100, 50, and 0 µl) of water were added to a system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. Tubes were taken out of the centrifuge, and aliquots of 100 µl for direct spectrophotometric analysis from the top and the bottom phases were withdrawn in duplicate and each diluted and mixed with appropriate reagents as indicated below and used for further analysis performed as described below.

The other aqueous two-phase system contained 8.88 wt. % Dextran-64 (molecular weight of about 64,000), 12.86 wt. % Ficoll-400 (molecular weight of about 400,000), and 0.01 M sodium phosphate buffer (pH 8.6). Each system was prepared by mixing the appropriate amounts of stock polymer, salt, and buffer solutions dispensed by liquid handling workstation Hamilton H-2200 into a microtube of a total volume of 1.2 mL up to a total volume of a system of 840 µL. A varied amount (40, 80, 120, and 160 µl) of the apo-transferrin solution or that of metal-transferrin and the corresponding amount (140, 100, 60, and 20 µl) of water were added to a system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. Tubes were taken out of the centrifuge, and aliquots of 100 µl for direct spectrophotometric analysis from the top and the bottom phases were withdrawn in duplicate and each diluted and mixed with appropriate reagents as indicated below and used for further analysis performed as described below.

The other aqueous two-phase system contained 8.88 wt. % Dextran-64 (molecular weight of about 64,000), 12.86 wt. % Ficoll-400 (molecular weight of about 400,000), 0.25 M $Na_2SO_4$, and 0.01 M sodium phosphate buffer (pH 8.6). Each system was prepared by mixing the appropriate amounts of stock polymer, salt, and buffer solutions dispensed by liquid handling workstation Hamilton ML-2200 into a microtube of a total volume of 1.2 mL up to a total volume of a system of 910 µL. A varied amount (20, 40, 60, and 90 µl) of the apo-transferrin solution or that of metal-transferrin and the corresponding amount (70, 50, 30, and 0 µl) of water were added to a system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. Tubes were taken out of the centrifuge, and aliquots of 100 µl for direct spectrophotometric analysis from the top and the bottom phases were withdrawn in duplicate and each diluted and mixed with appropriate reagents as indicated below and used for further analysis performed as described below.

The other aqueous two-phase system contained 8.88 wt. % Dextran-64 (molecular weight of about 64,000), 12.86 wt. % Ficoll-400 (molecular weight of about 400,000), 0.25 M $Li_2SO_4$, and 0.01 M sodium phosphate buffer (pH 8.6). Each system was prepared by mixing the appropriate amounts of stock polymer, salt, and buffer solutions dispensed by liquid handling workstation Hamilton H-2200 into a microtube of a total volume of 1.2 mL up to a total volume of a system of 920 µL. A varied amount (20, 40, 60, and 80 µl) of the apo-transferrin solution or that of metal-transferrin and the corresponding amount (60, 40, 20, and 0 µl) of water were added to a system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. Tubes were taken out of the centrifuge, and aliquots of 100 µl for direct spectrophotometric analysis from the top and the bottom phases were withdrawn in duplicate and each diluted and mixed with appropriate reagents as indicated below and used for further analysis performed as described below.

The other aqueous two-phase system contained 10.98 wt. % Dextran-64 (molecular weight of about 64,000), 15.95 wt. % Ficoll-400 (molecular weight of about 400,000), 0.13 M CsCl, and 0.01 M sodium phosphate buffer (pH 8.6). Each system was prepared by mixing the appropriate amounts of stock polymer, salt, and buffer solutions dispensed by liquid handling workstation Hamilton ML-2200 into a microtube of a total volume of 1.2 mL up to a total volume of a system of 920 µL. A varied amount (20, 40, 60, and 80 µl) of the apo-transferrin solution or that of metal-transferrin and the corresponding amount (60, 40, 20, and 0 µl) of water were added to a system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. Tubes were taken out of the centrifuge, and aliquots of 100 µl for direct spectrophotometric analysis from the top and the bottom phases were withdrawn in duplicate and each diluted and mixed with appropriate reagents as indicated below and used for further analysis performed as described below.

The other aqueous two-phase system contained 10.98 wt. % Dextran-64 (molecular weight of about 64,000), 15.95 wt. % Ficoll-400 (molecular weight of about 400,000), 0.13 M $NaClO_4$, and 0.01 M sodium phosphate buffer (pH 8.6). Each system was prepared by mixing the appropriate amounts of stock polymer, salt, and buffer solutions dispensed by liquid handling workstation Hamilton ML-2200 into a microtube of a total volume of 1.2 mL up to a total volume of a system of 920 µL. A varied amount (20, 40, 60, and 80 µl) of the apo-transferrin solution or that of metal-transferrin and the corresponding amount (60, 40, 20, and 0 µl) of water were added to a system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. Tubes were taken out of the centrifuge, and aliquots of 100 μl for direct spectrophotometric analysis from the top and the bottom phases were withdrawn in duplicate and each diluted and mixed with appropriate reagents as indicated below and used for further analysis performed as described below.

The other aqueous two-phase system contained 10.98 wt. % Dextran-64 (molecular weight of about 64,000), 15.95 wt. % Ficoll-400 (molecular weight of about 400,000), 0.24 M NaSCN, and 0.01 M sodium phosphate buffer (pH 8.6). Each system was prepared by mixing the appropriate amounts of stock polymer, salt, and buffer solutions dispensed by liquid handling workstation Hamilton ML-2200 into a microtube of a total volume of 1.2 mL up to a total volume of a system of 920 μL. A varied amount (20, 40, 60, and 80 μl) of the apo-transferrin solution or that of metal-transferrin and the corresponding amount (60, 40, 20, and 0 μl) of water were added to a system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. Tubes were taken out of the centrifuge, and aliquots of 100 μl for direct spectrophotometric analysis from the top and the bottom phases were withdrawn in duplicate and each diluted and mixed with appropriate reagents as indicated below and used for further analysis performed as described below.

For direct spectrophotometric analysis aliquots of 100 μl from the top and the bottom phases were withdrawn in duplicate and each mixed with 800 μl water. The protein concentrations in each phase were assayed by measuring the optical absorbance at 278 nm with a UV/VIS spectrophotometer HP-8530. The measured optical absorbance at 278 nm values of the diluted aliquots from the top phases were plotted as a function of the optical absorbance at 278 nm values of the similarly diluted aliquots from the bottom phases. The partition coefficient for the protein was determined as a slope of the linear curve representing the plot.

The partition coefficients for the examined proteins are given in Table 3. The data presented in Table 3 indicate clearly that there is a difference in the partitioning of apo-transferrin and transferrins saturated with different metals. The differences observed are due to different conformations of transferrins induced by binding of different metals. The data given in Table 3 also show that the changes in the partition coefficient value of a protein induced by binding of a binding partner depend on the particular two-phase system employed, although the changes are observed in any of the systems employed.

TABLE 3

Partition coefficients of human apo-transferrin and different metal-transferrins in different aqueous two-phase systems

| System* | Apo-Tf | $Fe^{3+}$ | $Al^{3+}$ | $Cu^{2+}$ | $Bi^{3+}$ | $Ca^{2+}$ |
|---|---|---|---|---|---|---|
| I    | 1.068 ± 0.021 | 0.655 ± 0.004 | 0.692 ± 0.001 | 0.717 ± 0.019 | 0.749 ± 0.007 | 0.759 ± 0.005 |
| II   | 1.305 ± 0.027 | 1.134 ± 0.014 | 1.038 ± 0.003 | 1.104 ± 0.012 | 1.121 ± 0.001 | 1.045 ± 0.002 |
| III  | 1.232 ± 0.008 | 1.152 ± 0.004 | 0.966 ± 0.010 | 1.075 ± 0.003 | 1.056 ± 0.002 | 1.012 ± 0.007 |
| IV   | 0.467 ± 0.013 | 0.514 ± 0.024 | 0.528 ± 0.001 | 0.537 ± 0.002 | 0.514 ± 0.002 | 0.570 ± 0.003 |
| V    | 0.247 ± 0.005 | 0.296 ± 0.002 | 0.319 ± 0.003 | 0.419 ± 0.009 | 0.345 ± 0.007 | — |
| VI   | 0.294 ± 0.003 | 0.321 ± 0.002 | 0.343 ± 0.004 | 0.403 ± 0.019 | 0.350 ± 0.007 | 0.401 ± 0.004 |
| VII  | 1.138 ± 0.020 | 0.961 ± 0.015 | 1.274 ± 0.018 | 1.068 ± 0.018 | — | — |
| VIII | 0.446 ± 0.015 | 0.243 ± 0.015 | 0.488 ± 0.005 | 0.459 ± 0.009 | — | — |

*Systems: I - Dex-Ficoll-buffer, pH 8.6; II - Dex-Ficoll-Na$_2$SO$_4$-buffer, pH 8.6; III - Dex-Ficoll-Li$_2$SO$_4$-buffer, pH 8.6; IV - Dex-Ficoll-CsCl-buffer, pH 8.6; V - Dex-Ficoll-NaClO$_4$-buffer, pH 8.6; VI - Dex-Ficoll-NaSCN-buffer, pH 8.6; VII - Dex-PEG-buffer, pH 7.01; VIII - Dex-PVP-buffer, pH 7.4

The data presented in Table 3 represent a structural signature corresponding to each ligand. This data could be visually displayed in several ways, some of which were outlined in the previous examples. Sometimes it is convenient to further reduce the complexity of the signature itself. One way to accomplish signature condensation is to calculate a (normalized) Euclidian distance for each signature versus a reference case. In the following we chose to describe the distance between each conformational state corresponding to each ligand, against that of the apo-Tf signature. One formula for calculating such distance is:

$$d_{i,j} = \sqrt{\sum_{k=1}^{n} \left( \frac{c_{j,k}}{\max(c_{,k})} - \frac{c_{i,k}}{\max(c_{,k})} \right)^2}$$

Where the distance is calculated between any signature j and the reference signature i, for n aqueous systems. Applying such distance measurement to the first 3 ligands in Table 4 produces the following data:

$Fe^{3+}$ to apo-Tf: 0.62

$Al^{3+}$ to apo-Tf: 0.54

$Cu^{2+}$ to apo-Tf: 0.64

The above data could be interpreted individually for each ligand as a measure of the overall similarity between the conformation induced by that ligand to that of the free receptor. Other data transformation and condensation methods could be readily devised, depending on the ultimate use of the signature. Thus, for example, if one wishes to rapidly compare the similarity of one ligand-induced conformation to another, or versus a reference state which might be that for a ligand whose biological activity is known, then the distance measure is one convenient way to express the similarity in a compact manner. Another application could be the use of the similarity distance to assess how close the signature of a particular isoform or a modified form or a biomolecule (e.g., with a single point mutation) to that of the intact biomolecule. Yet another possibility to use the distance measure of a signature similarity is to conveniently compare lots of microheterogeneous proteins (e.g., glycoproteins) that were produced using recombinant DNA techniques in non-mammalian host cells. In this case, the signature of each lot, representing the average conformation state of a mixture, could be readily compared against that obtained from a well-characterized lot of known biological activity level.

Example 4

In this example, it is shown how small differences in the primary structure of biomolecules, if they lead to significant changes in the conformation, can be detected using a signature.

β-Lactoglobulin A and β-lactoglobulin B from bovine milk were purchased from Sigma Chemical Company (St. Louis, Mo., USA) and used without further purification. The proteins differ by two amino acid residues—β-lactoglobulin A has Asp-residue in position 64 and Val-residue in position 118, while β-lactoglobulin B has Gly-residue in position 64 and Ala-residue in position 118. Stock solutions of β-lactoglobulin A and β-lactoglobulin B in water were prepared at the protein concentration of 5.0 mg/ml. Stock solution of β-lactoglobulin A and stock solution of β-lactoglobulin B were added to an aqueous two-phase system as described below.

The aqueous two-phase system contained 12.33 wt. % Dextran-64 (molecular weight of about 64,000), 6.05 wt. % PEG-6000 (molecular weight of about 6,000), 0.15M NaCl, and 0.01 M sodium phosphate buffer (pH 7.4). Each system was prepared by mixing the appropriate amounts of stock polymer, salt, and buffer solutions dispensed by liquid handling workstation Hamilton ML-2200 into a microtube of a total volume of 1.2 mL up to a total volume of a system of 800 µL. A varied amount (50, 100, 150, and 200 µl) of the each protein solution and the corresponding amount (150, 100, 50, and 0 µl) of water were added to a system. The ratio between the volumes of the two phases of each system of a final volume of 1.00 mL was as 1:1. The system was vigorously shaken and centrifuged for 30 min at about 4000 rpm in a centrifuge with a bucket rotor to speed the phase settling. Tubes were taken out of the centrifuge, and aliquots of 100 µl for direct spectrophotometric analysis from the top and the bottom phases were withdrawn in duplicate and each diluted and mixed with appropriate reagents as indicated below and used for further analysis performed as described below.

The other aqueous two-phase system contained 13.75 wt. % PEG-600 (molecular weight of about 600) and 21.00 wt. % sodium/potassium phosphate buffer (pH 6.8). Each system was prepared by mixing the appropriate amounts of stock polymer and buffer solutions dispensed by liquid handling workstation Hamilton ML-2200 into a microtube of a total volume of 1.2 mL up to a total volume of a system of 800 µL. A varied amount (40, 80, 120, 160, and 200 µl) of the each protein solution and the corresponding amount (160, 120, 80, 40, and 0.0 µl) of water were added to a system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. Tubes were taken out of the centrifuge, and aliquots of a given volume (100 µl for direct spectrophotometric analysis and 150 µl for fluorescence analysis) from the top and the bottom phases were withdrawn in duplicate and each diluted and mixed with appropriate reagents as indicated below and used for further analysis performed as described below.

The other aqueous two-phase system contained 12.33 wt. % Dextran-64 (molecular weight of about 64,000), 6.05 wt. % PEG-6000 (molecular weight of about 6,000), and 0.11 M sodium phosphate buffer (pH 7.4). Each system was prepared by mixing the appropriate amounts of stock polymer, salt, and buffer solutions dispensed by liquid handling workstation Hamilton ML-2200 into a microtube of a total volume of 1.2 mL up to a total volume of a system of 800 µL. A varied amount (50, 100, 150, and 200 µl) of the each protein solution and the corresponding amount (150, 100, 50, and 0 µl) of water were added to a system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. Tubes were taken out of the centrifuge, and aliquots of 100 µl for direct spectrophotometric analysis from the top and the bottom phases were withdrawn in duplicate and each diluted and mixed with appropriate reagents as indicated below and used for further analysis performed as described below.

The other aqueous two-phase system contained 12.33 wt. % Dextran-64 (molecular weight of about 64,000), 6.05 wt. % PEG-6000 (molecular weight of about 6,000), 0.1M $Li_2SO_4$, and 0.01 M sodium phosphate buffer (pH 7.4). Each system was prepared by mixing the appropriate amounts of stock polymer, salt, and buffer solutions dispensed by liquid handling workstation Hamilton ML-2200 into a microtube of a total volume of 1.2 mL up to a total volume of a system of 800 µL. A varied amount (50, 100, 150, and 200 µl) of the each protein solution and the corresponding amount (150, 100, 50, and 0 µl) of water were added to a system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. Tubes were taken out of the centrifuge, and aliquots of 100 µl for direct spectrophotometric analysis from the top and the bottom phases were withdrawn in duplicate and each diluted and mixed with appropriate reagents as indicated below and used for further analysis performed as described below.

The other aqueous two-phase system contained 12.33 wt. % Dextran-64 (molecular weight of about 64,000), 6.05 wt. % PEG-6000 (molecular weight of about 6,000), 0.1M NaSCN, and 0.01 M sodium phosphate buffer (pH 7.4). Each system was prepared by mixing the appropriate amounts of stock polymer, salt, and buffer solutions dispensed by liquid handling workstation Hamilton ML-2200 into a microtube of a total volume of 1.2 mL up to a total volume of a system of 800 µL. A varied amount (50, 100, 150, and 200 µl) of the each protein solution and the corresponding amount (150, 100, 50, and 0 µl) of water were added to a system. The ratio between the volumes of the two phases of each system of a final volume of 1.00 mL was as 1:1. The system was vigorously shaken and centrifuged for 30 min. at about 4000 rpm in a centrifuge with a bucket rotor to speed the phase settling. Tubes were taken out of the centrifuge, and aliquots of 100 µl for direct spectrophotometric analysis from the top and the bottom phases were withdrawn in duplicate and each diluted and mixed with appropriate reagents as indicated below and used for further analysis performed as described below.

For direct spectrophotometric analysis aliquots of 100 µl from the top and the bottom phases were withdrawn in duplicate and each mixed with 800 µl water. The protein concentrations in each phase were assayed by measuring the optical absorbance at 278 nm with a UV/VIS spectrophotometer HP-8530. The measured optical absorbance at 278 nm values of the diluted aliquots from the top phases were plotted as a function of the optical absorbance at 278 nm values of the similarly diluted aliquots from the bottom phases. The partition coefficient for the protein was determined as a slope of the linear curve representing the plot.

In addition, the protein concentrations in each phase were assayed by measuring the relative fluorescence intensity in wells of a 96-well microplate with a fluorescence microplate reader Bio-Tek F-6000 using excitation filter at 360 nm and emission filter at 460 nm. For this purpose aliquots of 50 μl from the top and the bottom phases were withdrawn, each mixed with 500 μl borate buffer, pH 8.4 and 75 μl fluorescamine solution (0.1 mg/ml) in acetone, maintained at ambient temperature for 15 min and used for further analysis. Aliquots of the mixtures (250 μl) were placed into wells of a microplate for fluorescence measurements. The measured fluorescence intensities of the aliquots from the top phases were plotted as a function of the fluorescence intensities of the aliquots from the bottom phases. The partition coefficient for a given protein was determined as a slope of the linear curve representing the plot.

The partition experiments were carried out in duplicate or triplicate. The partition coefficient values determined with two different assays agreed within 2-3% error range in each case.

The partition coefficients for the examined β-lactoglobulins A and B are presented in Table 4.

TABLE 4

Partition coefficient values for β-lactoglobulin A and β-lactoglobulin B from bovine milk in different aqueous two-phase systems.

| System | β-lactoglobulin A K-value | β-lactoglobulin B K-value |
| --- | --- | --- |
| PEG-600-NaPB | 3.596 ± 0.010 | 1.840 ± 0.006 |
| Dex-PEG-NaCl—NaPB | 0.048 ± 0.005 | 0.067 ± 0.003 |
| Dex-PEG-NaPB | 0.097 ± 0.011 | 0.123 ± 0.007 |
| Dex-PEG-Li$_2$SO$_4$—NaPB | 0.748 ± 0.015 | 0.404 ± 0.011 |
| Dex-PEG-NaSCN—NaPB | 0.096 ± 0.002 | 0.167 ± 0.013 |

This example illustrates that small difference in the protein 3-D structure, such as between β-lactoglobulin A and β-lactoglobulin B, in this case may be displayed as clearly different partition behavior pattern when a set of different two-phase systems is used. In a manner analogous to the previous examples, the signature could also be visualized, if so desired. Using such a set of different partition conditions provides information much more reliable and compelling than information obtainable with a single two-phase system.

Example 5

In this example, it is shown how small differences in the primary structure of biomolecules, if they lead to significant changes in the conformation, can be detected using a signature.

Human recombinant insulin was purchased from ICN Biomedicals Inc. (Aurora, Ohio, USA), bovine and porcine insulins were purchased from Calbiochem Corporation (San Diego, Calif., USA) and used without further purification. The proteins differ by two or three amino acid residues—human insulin has Thr-residue in position 8 and Ile-residue in position 10 in the A-chain, and Thr-residue in position 30 in the B-chain, while porcine insulin differs from human insulin by Ala-residue in position 30 in the B-chain, and bovine insulin has Ala-residue in position 8 and Val-residue in position 10 in the A-chain, and Ala-residue in position 30 in the B-chain. Stock solutions of all insulins in 0.009M HCl were prepared and titrated with 0.01M NaOH to pH ~6.0 with the final protein concentration of ca. 1.0 mg/ml. Stock solution of human insulin, stock solution of porcine insulin, and stock solution of bovine insulin were added to an aqueous two-phase system as described below.

The aqueous two-phase system contained 11.74 wt. % Dextran-69 (molecular weight of about 69,000), 17.51 wt. % Ficoll-70 (molecular weight of about 70,000) and 0.15M NaCl in 0.01 M sodium phosphate buffer (pH 7.4). Each system was prepared by mixing the appropriate amounts of stock polymer and buffer solutions dispensed by liquid handling workstation Hamilton ML-2200 into a microtube of a total volume of 1.2 mL up to a total volume of a system of 870 μL. A varied amount (0, 26, 52, 78, 104, and 130 μl) of each insulin solution and the corresponding amount (130, 104, 78, 52, 26, and 0 μl) of water were added to each system. The ratio between the volumes of the two phases of each system of a final volume of 1.00 mL was as 1:1. The system was shaken vigorously and centrifuged for 40 min. at about 4000 rpm to speed the resolution of the phases. Tubes were taken out of the centrifuge, and aliquots of a volume of 50 μl from the top and the bottom phases were withdrawn in duplicate and each diluted and mixed with appropriate reagents as indicated below and used for further analysis performed as described below.

The other aqueous two-phase system contained 13.67 wt. % Dextran-69 (molecular weight of about 69,000), 18.34 wt. % Ficoll-70 (molecular weight of about 70,000), 0.33M NaSCN, and 0.01 M sodium phosphate buffer (pH 7.4). Each system was prepared by mixing the appropriate amounts of stock polymer, salt, and buffer solutions dispensed by liquid handling workstation Hamilton ML-2200 into a microtube of a total volume of 1.2 mL up to a total volume of a system of 880 μl. A varied amount (0, 24, 48, 72, 96, and 120 μl) of each insulin solution and the corresponding amount (120, 96, 72, 48, 24, and 0 μl) of water were added to a system. The ratio between the volumes of the two phases of each system of a final volume of 1.00 mL was as 1:1. The system was vigorously shaken and centrifuged for 40 min. at about 4000 rpm in a centrifuge with a bucket rotor to speed the phase settling. Tubes were taken out of the centrifuge, and aliquots of 50 μl from the top and the bottom phases were withdrawn in duplicate and each diluted and mixed with appropriate reagents as indicated below and used for further analysis performed as described below.

The other aqueous two-phase system contained 12.16 wt. % Dextran-69 (molecular weight of about 69,000), 6.05 wt. % PEG-6000 (molecular weight of about 6,000), 0.43M NaClO$_4$, and 0.01 M sodium phosphate buffer (pH 7.4). Each system was prepared by mixing the appropriate amounts of stock polymer, salt, and buffer solutions dispensed by liquid handling workstation Hamilton ML-2200 into a microtube of a total volume of 1.2 mL up to a total volume of a system of 880 μl. A varied amount (0, 24, 48, 72, 96, and 120 μl) of each insulin solution and the corresponding amount (120, 96, 72, 48, 24, and 0 μl) of water were added to a system. The ratio between the volumes of the two phases of each system of a final volume of 1.00 mL was as 1:1. The system was vigorously shaken and centrifuged for 40 min. at about 4000 rpm in a centrifuge with a bucket rotor to speed the phase settling. Tubes were taken out of the centrifuge, and aliquots of 50 μl from the top and the bottom phases were withdrawn in duplicate and each diluted and mixed with appropriate reagents as indicated below and used for further analysis performed as described below.

The other aqueous two-phase system contained 12.16 wt. % Dextran-69 (molecular weight of about 69,000), 6.05 wt. % PEG-6000 (molecular weight of about 6,000), 1.26M NaSCN, and 0.01 M sodium phosphate buffer (pH 7.4). Each system was prepared by mixing the appropriate amounts of stock polymer, salt, and buffer solutions dispensed by liquid handling workstation Hamilton ML-2200 into a microtube of a total volume of 1.2 mL up to a total volume of a system of 880 µl. A varied amount (0, 24, 48, 72, 96, and 120 µl) of each insulin solution and the corresponding amount (120, 96, 72, 48, 24, and 0 µl) of water were added to a system. The ratio between the volumes of the two phases of each system of a final volume of 1.00 mL was as 1:1. The system was vigorously shaken and centrifuged for 40 min. at about 4000 rpm in a centrifuge with a bucket rotor to speed the phase settling. Tubes were taken out of the centrifuge, and aliquots of 50 µl from the top and the bottom phases were withdrawn in duplicate and each diluted and mixed with appropriate reagents as indicated below and used for further analysis performed as described below.

The protein concentrations in each phase were assayed by measuring the relative fluorescence intensity in wells of a 96-well microplate with a fluorescence microplate reader Bio-Tek F-6000 using excitation filter at 360 nm and emission filter at 460 nm. For this purpose aliquots of 50 µl from the top and the bottom phases were withdrawn, each mixed with 280 µl of o-phthaldialdehyde reagent solution (complete), placed into wells of a microplate for fluorescence measurements, shaken at ambient temperature for 2 min and the fluorescence measurements were performed. The measured fluorescence intensities of the aliquots from the top phases were plotted as a function of the fluorescence intensities of the aliquots from the bottom phases. The partition coefficient for a given protein was determined as a slope of the linear curve representing the plot.

The partition experiments were carried out in duplicate or triplicate. The partition coefficient values determined with two different assays agreed within 2-3% error range in each case.

The partition coefficients for the human, bovine, and porcine insulins are presented in Table 5.

TABLE 5

Partition coefficient values for human insulin, bovine insulin, and porcine insulin in different aqueous two-phase systems.

| System | Human Insulin K-value | Bovine Insulin K-value | Porcine Insulin K-value |
|---|---|---|---|
| Dex-Ficoll-NaCl—NaPB | 1.262 ± 0.010 | 1.512 ± 0.012 | 1.350 ± 0.015 |
| Dex-Ficoll-NaSCN—NaPB | 0.849 ± 0.014 | 0.968 ± 0.005 | 0.911 ± 0.006 |
| Dex-PEG-NaClO$_4$—NaPB | 0.776 ± 0.019 | 0.702 ± 0.024 | 0.656 ± 0.020 |
| Dex-PEG-NaSCN—NaPB | 1.898 ± 0.022 | 1.848 ± 0.021 | 1.514 ± 0.019 |

This example illustrates that small differences in the protein 3-D structure corresponding to human, bovine, and porcine insulins, are displayed via different partitioning behavior pattern when a set of different two-phase systems is used. In a manner analogous to the previous examples, the signature could also be visualized, if so desired. Since structural variations might exist within each insulin sample, the use of a signature comprised of information obtained from multiple systems provides a much more robust means to reliably distinguish or classify unknown samples.

Example 6

This example shows how the conformational signature can be used to assess the biological activity of an unknown drug, using signatures of known drugs as reference cases.

Sometimes, in the course of discovery of new drugs for a known target (e.g., a receptor), there are one or more previous drugs already available, with well-characterized biological efficacy profiles. Assuming that the biological activity of a receptor is reflected in its conformational state, then the problem at hand is how to use conformational information that is already available for previous drugs (ligands) for the same receptor to rapidly evaluate the anticipated biological activity of a new drug candidate. More generally, the question is how to predict a profile of conformationally-related bio-activities of a new drug candidate, if such profiles already exist for other drugs. Examples of conformationally-related bio-activities are biological activity level and toxicity, the latter expressed as a consequence of undesired binding to other receptors that produce conformational states that activate undesired biological activities. This particular embodiment is of significant value for analysis of many classes of receptors that undergo multiple conformational changes in response to bindings to different drugs. For example, many transcription factors, e.g., estrogen receptor, are known to exhibit multiple conformational states in response to binding to different estrogens. The discovery of new estrogens that modulate the estrogen receptor is of great current interest since it is widely recognized that the intermediate conformations are of practical interest for discovering new estrogens that exhibit favorable biological activity profile in various tissues in the body. Thus, instead of merely "turning on" the receptor upon binding, many drugs could be tailored to induce specific conformational states that could result in improved bio efficacy.

In the following hypothetical example we explore, using arbitrary numerical values, several methods that could be used to classify or predict the biological activity of an unknown drug for the same receptor. The techniques to experimentally obtain the numerical values that underlie the signature were already extensively demonstrated and discussed in previous examples.

Mathematically, the signature for each drug is a vector comprised of n values, each corresponding to a particular system. It is assumed that the signature corresponds to the conformational state, and that the conformational state is related to the biological activity of the receptor. If the bio-activity of the receptor, when bound to a specific drug is known, and could be classified numerically, e.g., using a normalized scale in comparison with other drugs (assigning 0 for pure antagonist and 10 for pure agonist), then the bio-activity could be mathematically related to the signature. The mathematical techniques that are used to relate the signature(s) to the bio-activity(ies) are, in general, referred to as mapping. These could be linear or nonlinear, could involve simple concepts as distance measures (in a manner similar to the measures shown for previous examples), are either local or global in range of validity, etc. The map is essentially a mathematical relationship between the input, represented by a vector of values, and the output, represented (typically) by a single value.

If only one signature and one biological activity measure are available, corresponding to one known drug, then a simple comparison of the two signatures (known and unknown drugs) is, in general, not sufficient to predict the bio-activity of the unknown drug. One exception is the case in which the two signatures are very similar, thus producing the same biological effect. If two drugs of known and different levels of bio-activities are available, then the signature for the unknown drug could be compared using, e.g., distance measurements to the two known signatures. The ratio between the two distances could be simply used as a ratio of the predicted bio-activity to both known activities. For example, if the three (normalized) signatures and their respective activities are:

| Drug | System | | | | Activity Level |
|---|---|---|---|---|---|
| | A | B | C | D | |
| X | 1 | 0.3 | 0.6 | 1 | 10 |
| Y | 0.5 | 0.6 | 1 | 0.7 | 0 |
| Z (unknown) | 0.7 | 1 | 0.8 | 0.9 | ? |

Using, e.g., the formula in Example 4, the distance of the signature of Z to the two known drugs, X and Y is:

Z–X: 0.79
Z–Y: 0.53

Thus, the bio-activity of Z is expected to be closer to Y by a factor of 0.79/0.53=1.5, and a simple calculation using that ratio shows the predicted activity to be 4. In a more general case, there will be multiple signatures and multiple bioactivity levels, but the same methodology could be followed. Other mapping alternatives, including matrix techniques, such as singular value decomposition, least squares, etc., could offer powerful and general tools for the same. For the instance for which there are many signatures available for the same receptor, other mapping and prediction options can be used. Non-linear regression, artificial neural networks, etc., could be used to construct the mapping. Once the mapping is known, it could be used with the signature vector of the unknown drug to predict its activity. The latter case is of specific value for modern drug discovery, in which the biological activity of many potential drugs is routinely measured, e.g., in cell-based assays or using animal models. Only few drug candidates (typically one) eventually are tested in clinical trials, but the previously available biological activity levels for many ligands that were not promoted to clinical trials could be used to develop a mapping of usefulness for predicting the activity of unknown drugs.

It is also possible to develop multiple signatures to several receptors of the same drug. Thus, it is possible to select the desired biological profile of a drug to multiple biological targets, using the methodologies described herein. Finally, it is also possible to derive multiple mappings between a given signature and multiple biological responses to predict the same for an unknown drug in a manner similar to the techniques described herein. For example, estrogenic compounds are known to produce a biological profile comprising of different activity levels in several tissues in the body. The design of SERM compounds (Selective Estrogen Receptor Modulators) attempts to optimize the biological profile, and the present methodology could be used for this or similar applications by considering several mappings of the same signature to different bio-activity levels.

Throughout this application, various publications are referenced. The disclosures of these publications in their entireties are hereby incorporated by reference into this application to more fully describe the state of the art to which this invention pertains. Furthermore, each reference is incorporated for the teachings contained therein which relate to the purpose for which it is cited as will be clear to anyone of skill in the art. Reference to these publications is not to be construed that they are prior art or that they disclose the invention as described herein.

While several embodiments of the invention have been described and illustrated herein, those of ordinary skill in the art will readily envision a variety of other means and structures for performing the functions and/or obtaining the results or advantages described herein, and each of such variations or modifications is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, if such features, systems, materials and/or methods are not mutually inconsistent, is included within the scope of the present invention.

In the claims (as well as in the specification above), all transitional phrases such as "comprising", "including", "carrying", "having", "containing", "involving", "composed of", "made of", "formed of" and the like are to be understood to be open-ended, i.e. to mean including but not limited to. Only the transitional phrases "consisting of" and "consisting essentially of" shall be closed or semi-closed transitional phrases, respectively, as set forth in the United States Patent Office Manual of Patent Examining Procedures, section 2111.03.

What is claimed is:

1. A method for determining the level of biological activity of a biomolecule that is bound to a binding partner, comprising:
   a) obtaining a reference signature of a biomolecule bound to a reference binding partner for which a reference level of biological activity is known by exposing the biomolecule and the reference binding partner to a plurality of interaction systems to determine a plurality of apparent partition coefficients, each interaction system comprising a plurality of components able to interact with the biomolecule, and constructing the reference signature by assembling the plurality of apparent partition coefficients into a numerical construct;
   b) determining a relationship between the reference signature of the biomolecule and the reference level of biological activity;
   c) obtaining an experimental signature of the biomolecule bound to an experimental binding partner by exposing the biomolecule and the experimental binding partner to a plurality of interaction systems to determine a plurality of apparent partition coefficients, each interaction system comprising a plurality of components able to interact with the biomolecule, and constructing the experimental signature by assembling the plurality of apparent partition coefficients into a numerical construct;
   d) comparing the experimental signature of c) and the relationship derived in b); and
   e) determining the level of biological activity of the experimental binding partner based on the comparison of d).

2. A method as in claim 1, wherein e) comprises ranking a relative degree of predicted activity in order with the reference level of biological activity of the reference binding partner.

3. A method as in claim 2, wherein e) comprises ranking on a relative scale to other binding partners.

4. A method as in claim 1, wherein the experimental binding partner is a candidate drug.

5. A method as in claim 1, wherein the reference signature comprises a plurality of numerical constructs for the same biomolecule in different tissue.

6. A method as in claim 1, wherein the reference signature comprises a plurality of numerical constructs for different biomolecules each determined when separately bound to the same reference binding partner in the same tissue.

7. A method as in claim 1, wherein the reference signature comprises a plurality of numerical constructs for different biomolecules each determined when separately bound to the same reference binding partner in different tissues.

8. A method as in claim 1, wherein the both the reference signature and the experimental signature are obtained in the presence of other biomolecules in the one or more interaction systems.

9. A method for determining the level of biological activity of a biomolecule that is bound to a binding partner, comprising:
   a) obtaining an experimental signature of a biomolecule bound to an experimental binding partner by exposing the biomolecule and the experimental binding partner to a plurality of interaction systems to determine a plurality of apparent partition coefficients, each interaction system comprising a plurality of components able to interact with the biomolecule, and constructing the experimental signature by assembling the plurality of apparent partition coefficients into a numerical construct;
   b) comparing the experimental signature with a reference signature of the biomolecule bound to a reference binding partner for which a reference level of biological activity is known; and
   c) determining the level of biological activity of the experimental binding partner based on the comparison of b).

10. The method of claim 9, wherein the reference signature of the biomolecule bound to the reference binding partner for which a reference level of biological activity is known is constructed by exposing the biomolecule and the reference binding partner to a plurality of interaction systems to determine a plurality of apparent partition coefficients, each interaction system comprising a plurality of components able to interact with the biomolecule, and constructing the reference signature by assembling the plurality of apparent partition coefficients into a numerical construct.

11. A method as in claim 9, wherein the experimental binding partner is a candidate drug.

12. A method as in claim 9, wherein the reference signature comprises a plurality of numerical constructs for the same biomolecule in different tissue.

13. A method as in claim 9, wherein the reference signature comprises a plurality of numerical constructs for different biomolecules each determined when separately bound to the same reference binding partner in the same tissue.

14. A method as in claim 9, wherein the reference signature comprises a plurality of numerical constructs for different biomolecules each determined when separately bound to the same reference binding partner in different tissues.

15. A method as in claim 9, wherein the both the reference signature and the experimental signature are obtained in the presence of other biomolecules in the one or more interaction systems.

16. A method as in claim 1, wherein the reference signature comprises a plurality of numerical constructs for different biomolecules each determined when separately bound to the same reference binding partner.

17. A method as in claim 9, wherein the reference signature comprises a plurality of numerical constructs for different biomolecules each determined when separately bound to the same reference binding partner.

* * * * *